United States Patent
Sarkar et al.

(10) Patent No.: US 9,801,805 B2
(45) Date of Patent: Oct. 31, 2017

(54) PERSONAL CARE COMPOSITION COMPRISING SILICONE NETWORK

(71) Applicant: Momentive Performance Materials Inc., Waterford, NY (US)

(72) Inventors: Alok Sarkar, Malda (IN); Anubhav Saxena, Bangalore (IN); Laxmi Samantara, Bangalore (IN); Ning Lu, Chappaqua, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 14/572,139

(22) Filed: Dec. 16, 2014

(65) Prior Publication Data

US 2016/0166495 A1    Jun. 16, 2016

(51) Int. Cl.
| | | |
|---|---|---|
| A61Q 19/00 | (2006.01) | |
| A61K 8/891 | (2006.01) | |
| A61K 8/04 | (2006.01) | |
| A61K 8/899 | (2006.01) | |

(52) U.S. Cl.
CPC .............. *A61K 8/891* (2013.01); *A61K 8/042* (2013.01); *A61K 8/899* (2013.01); *A61Q 19/00* (2013.01); *A61K 2800/10* (2013.01); *A61K 2800/95* (2013.01)

(58) Field of Classification Search
None
See application file for complete search history.

(56) References Cited

U.S. PATENT DOCUMENTS

| | | |
|---|---|---|
| 3,159,601 A | 12/1964 | Ashby |
| 3,159,662 A | 12/1964 | Ashby |
| 3,220,972 A | 11/1965 | Lamoreaux |
| 3,445,420 A | 5/1969 | Kookootsedes et al. |
| 3,715,334 A | 2/1973 | Karstedt |
| 3,775,452 A | 11/1973 | Karstedt |
| 3,814,730 A | 6/1974 | Karstedt |
| 4,256,870 A | 3/1981 | Eckberg |
| 4,279,717 A | 7/1981 | Eckberg et al. |
| 4,465,818 A | 8/1984 | Shirahata et al. |
| 4,562,096 A | 12/1985 | Lo et al. |
| 4,987,169 A | 1/1991 | Kuwata et al. |
| 5,128,431 A | 7/1992 | Riding et al. |
| 5,354,796 A | 10/1994 | Creecy et al. |
| 5,629,387 A | 5/1997 | Frances et al. |
| 5,654,362 A | 8/1997 | Schultz, Jr. et al. |
| 5,663,752 A | 9/1997 | Imamura et al. |
| 5,811,487 A | 9/1998 | Schultz, Jr. et al. |
| 6,296,869 B1 | 10/2001 | Crotty et al. |
| 6,423,322 B1 | 7/2002 | Fry |
| 6,531,540 B1 | 3/2003 | O'Brien |
| 7,381,769 B2 | 6/2008 | O'Brien |
| 7,687,574 B2 | 3/2010 | Lu et al. |
| 7,833,541 B2 | 11/2010 | Lu et al. |
| 8,697,829 B2 | 4/2014 | Saxena et al. |
| 8,703,881 B2 | 4/2014 | Saxena et al. |
| 2002/0188058 A1* | 12/2002 | Chaiyawat .............. A61K 8/02 524/588 |
| 2006/0052520 A1* | 3/2006 | O'Brien ................... A61K 8/02 524/588 |
| 2006/0052521 A1* | 3/2006 | O'Brien ................... A61K 8/02 524/588 |
| 2006/0079633 A1* | 4/2006 | O'Brien .................. A61K 8/042 524/588 |
| 2013/0171080 A1* | 7/2013 | Sarkar .................... A61K 8/899 424/59 |
| 2013/0172192 A1* | 7/2013 | Saxena .................. C08G 77/14 504/360 |
| 2013/0172193 A1* | 7/2013 | Saxena .................. A01N 25/10 504/360 |
| 2013/0172419 A1* | 7/2013 | Saxena .................. C08G 77/38 514/570 |
| 2013/0172427 A1* | 7/2013 | Saxena ................. C09D 183/08 514/772.1 |
| 2013/0172510 A1 | 7/2013 | Saxena et al. |
| 2014/0017188 A1* | 1/2014 | Sarkar .................... A61K 8/899 424/64 |

FOREIGN PATENT DOCUMENTS

| | | |
|---|---|---|
| JP | 06-247835 | 2/1993 |
| JP | 06-247827 | 9/1994 |
| WO | 00/08087 A1 | 2/2000 |

OTHER PUBLICATIONS

J.L. Spier, "Homogeneous Catalysis of Hydrosilation by Transition Metals, in Advances in Organometallic Chemistry", vol. 17, (1979) pp. 407-447, F.G.A. Stone & R. West Editors, Academic Press.
U.S. Appl. No. 14/572,132 for Applicants Anubhav Saxena et al. filed Dec. 16, 2014.
U.S. Appl. No. 14/572,118 for Applicants Monjit Phukan et al. filed Dec. 16, 2014.
U.S. Appl. No. 14/572,108 for Applicants Monjit Phukan et al. filed Dec. 16, 2014.
International Search Report and Written Opinion dated Mar. 14, 2016.

* cited by examiner

*Primary Examiner* — Robert S Loewe
(74) *Attorney, Agent, or Firm* — Joseph S. Ostroff

(57) ABSTRACT

The invention is directed to a personal care composition which contains a crosslinked ionic silicone network wherein the crosslinked ionic silicone network is formed by the ring-opening polymerization of oxirane moiety.

23 Claims, 1 Drawing Sheet

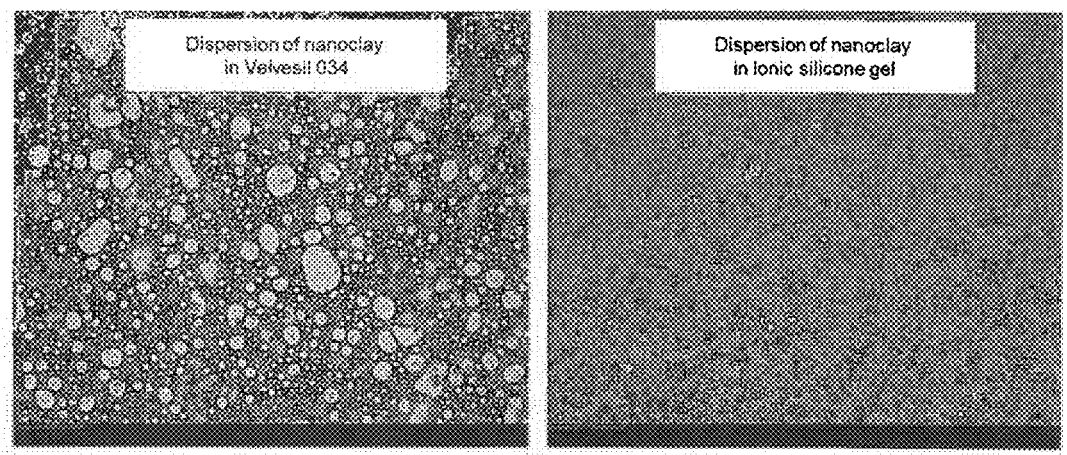

PERSONAL CARE COMPOSITION COMPRISING SILICONE NETWORK

FIELD OF THE INVENTION

The present invention relates to silicone polymers, specifically silicone polymer networks that can provide improved sensory benefits in personal care compositions and the resultant personal care applications.

BACKGROUND OF THE INVENTION

The personal care industry thrives on being able to deliver multiple performance products based on mixtures of several components, with each having performance characteristics important to or desirable in the final formulation. One desirable characteristic is the ability to provide a silky initial feel in the formulation.

Silicone copolymer gels are known in the personal care industry for many uses including their use in skin care applications. However these gels often fail to provide the desired degree of wash-off resistance, pigment dispersibility and anti-whitening properties.

In addition, such silicone copolymer gels have typically been made by the hydrosilylation reactions, which require the use of both Si—H functional groups and terminal olefinic groups to form crosslinked siloxane polymers. Thus, only siloxane structures that incorporate silyl hydride groups and optionally, vinyl functional siloxane groups, can be utilized in making these materials. This method of generating crosslinked siloxane polymers limits the range of desirable organofunctional groups that may be incorporated into the polymeric structure to create additional performance advantages in complex formulations.

SUMMARY OF THE INVENTION

The invention is directed to a personal care composition which contains an ionically-modified cross-linked silicone network. The ionically-modified cross-linked silicone network is chosen from cross-polymers formed by the ring-opening polymerization of a oxirane-functional compound (silicone-non-silicone) in the presence of hydride-functional silicone, a precious metal catalyst and optionally a solvent and, wherein one or more of the oxirane-functional compound (silicone or non-silicone), the hydride functional silicone, or the ring-opening polymerization neutral solvent contains ionic radical moiety.

In one embodiment herein there is provided a personal care composition comprising at least an oil phase, wherein the personal care composition is made by the process comprising adding an ionically-modified cross-linked silicone network gel to the oil phase of the personal care composition which the ionically-modified cross-linked silicone network gel is derived from reacting
i) at least one oxirane-functionalized compound;
ii) an oxirane ring-opening polymerization catalyst;
iii) a carrier solvent; and,
iv) optionally, one or more silicon hydride activators,
wherein at least one of (i), (iii) or (iv) comprises a silicone of formula (I):

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$
where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to 60 carbon atoms;
where $R^4, R^{12}, R^{17}$ are monovalent or multivalent radical bearing ionic group(s).
where $R^7, R^{14}$ and $R^{18}$ are independently selected from hydrogen, —$OR^{20}$ or hydrosilylation effective unsaturated monovalent radicals, wherein $R^{20}$ is selected from hydrogen and monovalent hydrocarbon radicals of from 1 to 60 carbon atoms,
where the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than 0, and wherein either at least one of (i) and (iii) comprises hydride moiety or if (i) and (iii) do not comprise hydride moiety, then (iv) is present, and
wherein the crosslinked ionic silicone network is formed by the ring-opening polymerization of oxirane moiety with hydride moiety; and,
shearing the crosslinked ionic silicone network during and/or after the polymerization step with at least carrier solvent (iii) to form the crosslinked ionic silicone network gel.

In one other embodiment herein there is provided a process of preparing a personal care composition comprising at least an oil phase, wherein the personal care composition is made by the process comprising adding an ionically-modified cross-linked silicone network gel to the oil phase of the personal care composition which the ionically-modified cross-linked silicone network gel is derived from reacting:
i. an oxirane-functionalized compound;
ii. an oxirane ring-opening polymerization catalyst; and
iii. a carrier solvent; and,
iv. optionally, one or more silicon hydride activators,
subject to the limitation that at least (i), (iii) or (iv) comprises the ionically modified silicone of general formula (I) as defined herein, and
wherein the crosslinked ionic silicone network is formed by the ring-opening polymerization of oxirane moiety; and,
shearing the crosslinked ionic silicone network during and/or after the polymerization step with at least carrier solvent (iii) to form the crosslinked ionic silicone network gel.

BRIEF DESCRIPTION OF THE DRAWING

FIG. 1 shows optical microscope images of examples CF3 and F5

DETAILED DESCRIPTION OF THE INVENTION

The inventors herein have unexpectedly discovered a personal care composition which contains a crosslinked ionic silicone network gel in the oil phase of the personal care composition which gel is formed by the polymerization of silicone polymer(s) which can contain one or more of oxirane moiety, silyl hydride moiety and ionic radicals (and the other components described herein) in the presence of catalyst and carrier solvent, which gel is provided by shearing with the carrier solvent during and/or after polymerization. The gel used in the oil phase of the personal care composition can provide for good sensory benefits, e.g., a silky feel, while also providing the desired degree of wash-off resistance, pigment dispersibility and anti-whitening properties. The crosslinked ionic silicone network gel is formed by the ring-opening polymerization of oxirane moiety with hydride moiety without the formation of polyether moieties or polyether crosslinks.

As used herein, the expression "ionically-modified cross-linked silicone network composition" can comprise the reaction product of the oxirane-functionalized polymers (silicone or non-silicone) with hydride silicone in the presence of the solvent and oxirane ring-opening catalyst and is used interchangeably with the expression "ionically-modified silicone cross-polymer".

It will be understood herein that the formation of the ionically-modified crosslinked silicone network can be provided by reaction of a (a) ionically modified silicone containing at least one oxirane and at least one silyl-hydride group, (b) ionically modified polymer containing at least one oxirane group and a hydride silicone, (c) a non-ionic polymer containing at least one oxirane group and an ionically modified hydride silicone, (d) a solvent, optionally containing ionic groups, and (e) a catalyst, wherein any one or more of (a), (b), (c), and optionally (d) contains ionic groups as described herein.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example particulate solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

In one non-limiting embodiment herein the crosslinked ionic silicone network can be in the absence of polyether moieties and/or polyether crosslinks. More specifically, the crosslinked ionic silicone network can be in the absence of one or more moieties selected from glycolide, lactide, butyrolactide and caprolactide. In yet a further non-limiting embodiment herein, the crosslinked ionic silicone network can be in the absence of acrylate and/or olefinic functionality. In yet a further non-limiting embodiment, the crosslinked ionic silicone network is in the absence of olefinic and hydride crosslinking.

It will be understood herein that the expression "oil phase" shall mean that this portion of the personal care composition contains one substantially water-insoluble component, optionally a plurality of substantially water-insoluble components. Here, substantially water-insoluble means that the solubility of the components in water alone or as a mixture is less than 10 g/100 g of water, preferably less than 1 g/100 g of water, particularly preferably less than 0.1 g/100 g of water, measured at 20.degree. C., and the pressure of the ambient atmosphere, i.e. from 900 to 1100 hPa. In the case of the oil phase of the personal care composition according to the invention, the viscosity of the oil phase, measured at 20.degree. C. and a shear gradient of 10 sec$^{-1}$, is from 0.1 to 1,000,000 mPas, preferably from 0.1 to 500,000 mPas, particularly preferably from 0.2 to 100,000 mPas. In the case of the emulsion according to the invention, the oil phase can preferably contain a plurality of components. The individual components may be both substances which are liquid at 20.degree. C. and solids, the total mixture of the individual components having the above-mentioned viscosity. Preferably, but not necessarily, a multicomponent oil phase is a true solution, i.e. a homogeneous phase in which no further phase interfaces occur.

In addition to water, the aqueous phase (which is the other of the two phases present in the personal care composition) may contain further components, such as, preferably, acids, bases, salts, water-soluble organic compounds, such as alcohols, carboxylic acids and derivatives thereof, amines or other organic compounds, polymeric or oligomeric compounds, such as polyols or polyamines or polyamidoamines, complex water-soluble organic compounds, such as cosmetic active substances, dyes, organo-element compounds, such as water-soluble organosilicon compounds or water-soluble transition metal compounds. Optionally, the aqueous phase may contain water-wettable particles, such as pigments, fillers or rheological additives.

The expression "shearing" as used herein is understood to mean either the silicone composition may be further processed to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus and other methods known in the art. Optionally, one or more fluids may be added to the personal care composition prior to the shearing.

It will be understood herein that at rest, the crosslinked ionic silicone network gel exhibits the properties of a solid gel material. The gel of the present invention exhibits high stability and resistance to syneresis, that is, the composition exhibits little or no tendency for fluid to flow from the composition and imparts high stability and syneresis resistance to personal care compositions which include the gel as a component in the oil phase. The high stability and syneresis resistance persists with prolonged aging of such personal care compositions and personal care applications containing such compositions. However, fluid may be released from the network by subjecting the silicone composition to a shearing force, such as, for example, by rubbing the composition between one's fingers, to provide improved sensory feel characteristic of the fluid component of the personal care composition.

In another embodiment there is provided a personal care composition comprising an oil phase and an aqueous phase which personal care composition is made by the process of adding at least one ionically-modified cross-linked silicone network gel to the oil phase of the personal care composition, and wherein the said cross-linked network gel comprises an ionically modified organo-silicone with the general formula:

$$M^1{}_a M^2{}_b M^3{}_c D^1{}_d D^2{}_e D^3{}_f T^1{}_g T^2{}_h T^3{}_i Q_j \qquad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are aliphatic, aromatic or fluoro containing monovalent hydrocarbon radicals containing from 1 to about 60 carbon atoms, specifically from 1 to about 20 carbon atoms, and more specifically from 1 to about 8 carbon atoms, and in some embodiment, the aforestated ranges can have lower limits of 2 or 3 carbon atoms;

where $R^4$, $R^{12}$, $R^{17}$ are monovalent or multivalent radical bearing ionic group(s).

where $R^7$, $R^{14}$ and $R^{18}$ are independently selected from hydrogen, —OR$^{20}$ or unsaturated monovalent radicals wherein the unsaturated monovalent radicals contain from 2 to 60 carbon atoms, more specifically from 2 to about 20 carbon atoms, and most specifically from 2 to about 8 carbon atoms, and wherein each $R^{20}$ is independently selected from hydrogen, monovalent hydrocarbon radicals of from 1 to about 60 carbon atoms specifically from 1 to about 20 carbon atoms, more specifically from 1 to about 8 carbon atoms and in some embodiments, the aforestated ranges of unsaturated monovalent radicals or range of monovalent hydrocarbon radicals in R$^{20}$ can have lower limits of 2 or 3 carbon atoms, where the subscript a, b, c, d, e, f, g, h, i, j are zero or positive subject to the following limitations: the sum a+b+c+d+e+f+g+h+i+j is greater than or equal to 2 and less than or equal to 6000, specifically a+b+c+d+e+f+g+h+i+j is greater than or equal to 2 and less than or equal to 4000, more specifically a+b+c+d+e+f+g+h+i+j is less than or equal to 2000, and in some embodiments the aforestated ranges of a+b+c+d+e+f+g+h+i+j can have lower limits of any one of 3, 4, 5, 10, 12, 18, 20, 30 and 50 as well as 100, 200, 300 and 500, b+e+h is greater than 0, more specifically b+e+h is greater than 1, even more specifically b+e+h is greater than 2, and yet more specifically b+e+h is from 1 to about 100, further more specifically from 1 to about 50 and most specifically from 1 to about 10, wherein the stated ranges for b+e+h can in some embodiments have lower endpoints of any one of 2, 3, 4, 5, 10, 50 or 100, and wherein the crosslinked ionic silicone network is formed by the ring-opening polymerization of oxirane moiety with hydride moiety and more specifically, wherein the crosslinked ionic silicone network is in the absence of polyether moieties or polyether crosslinks, wherein the gel is formed by the shearing of the network during and/or after the ring-opening polymerization.

In a preferred embodiment, the ionically-modified crosslinked silicone network comprising the ionically modified silicone of formula (I), wherein the monovalent ionic radicals $R^4$, $R^{12}$, $R^{17}$ are selected from the formula (II):

$$\text{-A-I}^{x-}M_n{}^{y+}; \qquad (II)$$

where A is a spacing group having selected from a divalent hydrocarbon and hydrocarbonoxy group each containing from 1 to about 60 carbon atoms, more specifically from 1 to 20 carbon atoms, and most specifically from 1 to about 8 carbon atoms, and in some embodiments, the aforestated ranges of the divalent hydrocarbon and hydrocarbonoxy group can have lower limits of 2 or 3 carbon atoms, wherein the hydrocarbonoxy group contains at least one oxygen heteroatom, where superscripts x and y are positive integers such as where x and y are independently from/to 6, more specifically from 1 to 3, such to the proviso that and x is a product of n and y, and each subscript n independently has a value of from 1 to 6, more specifically from 1 to about 3, where I is an ionic group such as sulfonate —$SO_3^-$, sulfate —$OSO_3^-$, carboxylate —$COO^-$, phosphonate —$PO_3^{2-}$ and phosphate —$OPO_3^{2-}$ group, more specifically sulfonate —$SO_3^-$, where M is hydrogen or a cation independently selected from alkali metals, alkaline earth metals, rare earth metals, transition metals, metals, metal complexes, quaternary ammonium, polymeric cations and phosphonium groups.

In another preferred embodiment, wherein the ionically-modified cross-linked silicone network comprising the ionically modified silicone of formula (I), wherein the monovalent radicals $R^4$, $R^{12}$, $R^{17}$ are selected from zwitterions having the formula (III):

$$—R'—NR''_2{}^+—R'''—I \qquad (III)$$

where R' is a divalent hydrocarbon radical containing from 1 to about 60 carbon atoms, specifically from 1 to about 20 carbon atoms, and more specifically from 1 to about 8 carbon atoms, and in some embodiment, the aforestated ranges for R' can have lower limits of 2 or 3 carbon atoms, and where R'' is monovalent hydrocarbon radical containing from 1 to about 60 carbon atoms, specifically from 1 to about 20 carbon atoms and more specifically from 1 to about 8 carbon atoms, and optionally, one or more of a sulfur atom, a nitrogen atom, oxygen atom, and in some embodiments, the aforestated ranges for R'' can have lower limits of 2 or 3 carbon atoms, and where R''' is divalent hydrocarbon radical containing from 2 to about 20 carbon atoms, specifically from 2 to about 8 carbon atoms and more specifically from 2 to about 4 carbon atoms; and, I is an ionic group such as sulfonate —$SO_3^-$, sulfate —$OSO_3^-$, carboxylate —$COO^-$, phosphonate —$PO_3^{2-}$ group and phosphate —$OPO_3^{2-}$ group.

In a preferred embodiment, the personal care composition comprises an ionically-modified cross-linked silicone network gel added to the oil phase of the personal care composition, wherein the said cross-linked network gel is derived from the ring-opening polymerizing of:
  i. at least one oxirane-functionalized compound (silicone or non-silicone).
  ii. an oxirane ring-opening polymerization catalyst,
  iii. a carrier solvent, and
  iv. optionally, one or more silicon hydride activators; subject to the limitation that at least one of (i), (iii) or (iv) comprises the ionically modified silicone of general formula (I) and wherein the crosslinked ionic silicone network is formed by the ring-opening polymerization of oxirane moiety, and during and/or after the ring-opening polymerization shearing the ionically-modified crosslinked silicone network in the presence of at least the carrier solvent (iii) to form the gel.

In a more preferred embodiment herein, the crosslinked ionic silicone network (which can be sheared in the presence of a solvent to form a gel thereof) comprises the epoxy ring-opening polymerization reaction product of:

a. an ionically modified silicone containing oxirane with general formula (IV):

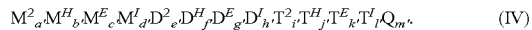

$$M^2{}_a M^H{}_b M^E{}_c M^I{}_d D^2{}_e D^H{}_f D^E{}_g D^I{}_h T^2{}_i T^H{}_j T^E{}_k T^I{}_l Q_{m'}. \qquad (IV)$$

wherein:
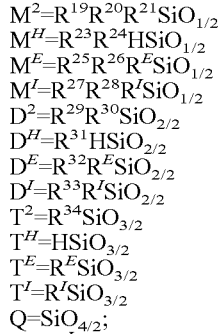
$M^2 = R^{19} R^{20} R^{21} SiO_{1/2}$
$M^H = R^{23} R^{24} HSiO_{1/2}$
$M^E = R^{25} R^{26} R^E SiO_{1/2}$
$M^I = R^{27} R^{28} R^I SiO_{1/2}$
$D^2 = R^{29} R^{30} SiO_{2/2}$
$D^H = R^{31} HSiO_{2/2}$
$D^E = R^{32} R^E SiO_{2/2}$
$D^I = R^{33} R^I SiO_{2/2}$
$T^2 = R^{34} SiO_{3/2}$
$T^H = HSiO_{3/2}$
$T^E = R^E SiO_{3/2}$
$T^I = R^I SiO_{3/2}$
$Q = SiO_{4/2}$;

where $R^I$ is ionic group described by structure (II) and (III), and $R^E$ is independently a monovalent hydrocarbon radical containing at least one oxirane moiety, which contains from 2 to about 60 carbon atoms, more specifically from about 2 to about 30 carbon atoms, more specifically from about 2 to about 20 carbon atoms and in some embodiments the aforestated ranges for $R^E$ can have lower limits of 2 or 3 carbon atoms, b. an oxirane ring-opening catalyst,
c. a carrier solvent for swelling the crosslinked network; and,
d. optionally, one or more silicon hydride activators,
wherein $R^{19}$, $R^{20}$, $R^{21}$, $R^{29}$, $R^{30}$ and $R^{34}$ are independently monovalent hydrocarbon radicals having from one to sixty carbon atoms, specifically from 1 to about 20 carbon atoms, and more specifically from 1 to about 8 carbon atoms, and in some embodiment, the aforestated ranges for $R^{19}$, $R^{20}$, $R^{21}$, $R^{29}$, $R^{30}$ and $R^{34}$ can have lower limits of 2 or 3 carbon atoms;

$R^{23}$, $R^{24}$ and $R^{31}$ are independently hydrogen, or monovalent hydrocarbon radicals having from one to sixty carbon atoms specifically from 1 to about 20 carbon atoms, and more specifically from 1 to about 8 carbon atoms, and in some embodiment, the aforestated ranges for $R^{23}$, $R^{24}$ and $R^{31}$ can have lower limits of 2 or 3 carbon atoms;

$R^{25}$, $R^{26}$ and $R^{32}$ are independently $R^E$ or monovalent hydrocarbon radicals having from one to sixty carbon atoms specifically from 1 to about 20 carbon atoms, and more specifically from 1 to about 8 carbon atoms, and in some embodiment, the aforestated ranges for $R^{25}$, $R^{26}$ and $R^{32}$ can have lower limits of 2 or 3 carbon atoms, wherein each $R^E$ is independently a monovalent hydrocarbon radical containing at least one oxirane moiety and having from two to sixty carbon atoms specifically from 2 to about 30 carbon atoms, and more specifically from 2 to about 20 carbon atoms;

$R^{27}$, $R^{28}$ and $R^{33}$ are independently $R^I$ or monovalent hydrocarbon radicals having from one to sixty carbon atoms more specifically from 1 to about 20 carbon atoms, and more specifically from 1 to about 8 carbon atoms, and in some embodiment, the aforestated ranges for $R^{27}$, $R^{28}$ and $R^{33}$ can have lower limits of 2 or 3 carbon atoms and wherein $R^I$ is an ionic group as defined herein, e.g., a group of formula (II) or (III);

and where the stoichiometric subscripts a', b', c', d', e', f', g', h', i', j', k', l' and m' are either zero or positive subject to the following limitations: c'+g'+k'>1, more specifically c'+g'+k'>2 and in some embodiments c'+g'+k' is from about 2 to about 250, more specifically from 2 to about 100 and most specifically from 2 to about 25, which ranges of c'+g'+k' can have lower endpoints of any one of 3, 4, 5, 10, 50 or 100; d'+h'+l'>1, more specially d'+h'+l'>2 and even more specifically d'+h'+l' is from about 1 to about 100, more specifically from 1 to about 50 and most specifically from 1 to about 10, and wherein the stated ranges for d'+h'+l' can have lower endpoints of any one of 2, 3, 4, 5, 10, 50 or 100; b'+f'+j' if present is greater than c'+g'+k'; 3≥a'+b'+c'+d'+e'+f'+g'+h'+i'+j'+k'+l'+m'≤6000, more specifically 3≥a'+b'+c'+d'+e'+f'+g'+h'+i'+j'+k'+l'+m'≤4000 and most specifically 3≥a'+b'+c'+d'+e'+f'+g'+h'+i'+j'+k'+l'+m'≤2000, and in some embodiments the aforestated ranges of a'+b'+c'+d'+e'+f'+g'+h'+i'+j'+k'+l'+m' can have lower limits of any one of 3, 4, 5, 10, 12, 18, 20, 30 and 50 as well as 100, 200, 300 and 500; and, with the proviso b'+f'+j'>1 when silicone hydride activator (a) is absent and wherein the crosslinked ionic silicone network is formed by the ring-opening polymerization of oxirane moiety and more specifically, wherein the crosslinked ionic silicone network is in the absence of polyether moieties or polyether crosslinks.

In a preferred embodiment, the personal care composition comprising crosslinked ionic silicone network gel in the oil phase thereof is such that, wherein the said cross-linked ionic silicone network (used to make the gel) is derived from reaction product of (VI) (a silicon hydride activator):

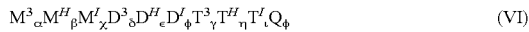   (VI)

wherein:
$M^3 = R^{35}R^{36}R^{37}SiO_{1/2}$
$M^H = R^{38}R^{39}HSiO_{1/2}$
$M^I = R^{40}R^{41}R^I SiO_{1/2}$
$D^3 = R^{42}R^{43}SiO_{2/2}$
$D^H = R^{44}HSiO_{2/2}$
$D^I = R^{45}R^I SiO_{2/2}$
$T^3 = R^{46}SiO_{3/2}$
$T^H = HSiO_{3/2}$
$T^I = R^I SiO_{3/2}$
$Q = SiO_{4/2}$; and, (i) one or more oxirane containing molecules,
(ii) an oxirane ring-opening polymerization catalyst; and,
(iii) a solvent for swelling the said cross-linked network, where
$R^{35}$, $R^{36}$, $R^{37}$, $R^{42}$, $R^{43}$ and $R^{46}$ are independently monovalent hydrocarbon radicals having from one to sixty carbon atoms, specifically from 1 to about 20 carbon atoms, and more specifically from 1 to about 8 carbon atoms, and in some embodiment, the aforestated ranges for $R^{35}$, $R^{36}$, $R^{37}$, $R^{42}$, $R^{43}$ and $R^{46}$ can have lower limits of 2 or 3 carbon atoms;

$R^{38}$, $R^{39}$ and $R^{44}$ are independently hydrogen or monovalent hydrocarbon radicals having from one to sixty carbon atoms specifically from 1 to about 20 carbon atoms, and more specifically from 1 to about 8 carbon atoms, and in some embodiment, the aforestated ranges for $R^{38}$, $R^{39}$ and $R^{44}$ can have lower limits of 2 or 3 carbon atoms;

$R^{40}$, $R^{41}$ and $R^{45}$ are independently $R^I$ or monovalent hydrocarbon radicals having from one to sixty carbon atoms specifically from 1 to about 20 carbon atoms, and more specifically from 1 to about 8 carbon atoms, and in some embodiment, the aforestated ranges for $R^{40}$, $R^{41}$ and $R^{45}$ can have lower limits of 2 or 3 carbon atoms, where R' is as defined herein, i.e., an ionic group as defined herein, e.g., a group of formula (II) or (III), and where the stoichiometric subscripts α, β, χ, δ, ε, φ, γ, η, ι and φ are either zero or positive subject to the following limitations: 2≥α+β+χ+δ+ε+φ+γ+η+ι+φ≤6000, more specifically 2≥α+β+χ+δ+ε+φ+γ+η+ι+φ≤4000 and most specifically 2≥α+β+χ+δ+ε+φ+γ+η+ι+φ≤2000, and in some embodiments the aforestated ranges of α+β+χ+δ+ε+φ+γ+η+ι+φ can have lower limits of any one of 3, 4, 5, 10, 12, 18, 20, 30 and 50 as well as 100, 200, 300 and 500; β+ε+η>1, more specifically β+ε+η≥2, and in some embodiments, β+ε+η is from 2 to about 250, more specifically from about 2 to about 100 and most specifically from about 2 to about 25, and wherein in some embodiments said ranges of β+ε+η can have lower endpoints of any one of 3, 4, 5, 10, 50 or 100; and χ+φ+ι≥0 more specifically χ+φ+ι>2 and even more specifically χ+φ+ι is from about 1 to about 100, more specifically from 1 to about 50 and most specifically from 1 to about 10, and wherein the stated ranges for χ+φ+ι can have lower endpoints of any one of 2, 3, 4, 5, 10, 50 or 100, and wherein the crosslinked ionic silicone network is formed by the ring-opening polymerization of oxirane moiety and more specifically, wherein the crosslinked ionic silicone network is in the absence of polyether crosslinks.

In yet another more preferred embodiment, the said crosslinked ionic silicone network (which can be made into a gel by use of shear and solvent as described herein, which gel may be for use in the oil phase of a personal care composition) comprises the reaction product of:
(i) at least one oxirane functionalized compound (silicone or non-silicone).
(ii) an oxirane ring-opening polymerization effective catalyst;
(iii) a solvent for swelling the crosslinked ionic silicone network which has the general formula (V):

   (V)

wherein:
$M^3 = R^1R^2R^3SiO_{1/2}$
$M^4 = R^4R^5R^I SiO_{1/2}$
$D^3 = R^6R^7SiO_{2/2}$
$D^4 = R^8R^I SiO_{2/2}$
$T^3 = R^9 SiO_{3/2}$
$T^4 = R^{10} SiO_{3/2}$
$Q = SiO_{4/2}$, and wherein, the radicals $R^1$, $R^2$, $R^3$, $R^4$, $R^5$, $R^6$, $R^7$, $R^8$, $R^9$ and $R^{10}$ are independently selected from aliphatic or aromatic monovalent hydrocarbon radicals having from 1 to 60 carbon atoms, more specifically from 1 to 30 carbon atoms, more specifically from 1 to 12 carbon atoms and most specifically from 1 to 6 carbon atoms, and optionally each independently containing at least one hetero atom, and in some embodiments, the stated ranges for $R^1$, $R^2$, $R^3$, $R^4$, $R^5$, $R^6$, $R^7$, $R^8$, $R^9$ and $R^{10}$ can have lower limits of 2 or 3, and the subscripts α', β', χ', δ', ε', φ', and γ' are zero or positive subject to the following limitations: 2≤α'+β'+χ'+δ'+ε'+φ'+γ'≤6000, more specifically 2≤α'+β'+χ'+δ'+ε'+φ'+γ'≤4000, and most specifically 2≤α'+β'+χ'+δ'+ε'+φ'+γ'≤2000 and the aforestated ranges for α'+β'+χ'+δ'+ε'+φ'+γ' can have lower limits of any one of 3, 4, 5, 10, 12, 18, 20, 30 and 50 as well as 100, 200, 300 and 500; and, β'+δ'+φ'>0, more specifically, more specifically β'δ'+φ'>2 and even more specifically β'+δ'+φ' is from about 1 to about 100, more specifically from 1 to about 50 and most specifically from 1 to about 10, and wherein the stated ranges for β'+δ'+φ' can have lower endpoints of any one of 2, 3, 4, 5, 10, 50 or 100; and, (iv) optionally at least one or more silicon hydride activators.

It will be understood herein that formulae (IV), (V) and (VI) can be more specific embodiments of general formula (I) as described herein.

It will be understood herein that any of the embodiments described herein can be revised accordingly such that the crosslinked ionic silicone network, the gel formed therefrom, and personal care compositions containing the same can be formed (and comprise) by combinations of reactants (with the solvent not being a reactant but contained within the reaction product of crosslinked ionic silicone network composition) of any of the following:

ionic oxirane containing hydride-silicone, and non-ionic oxirane compound (silicone or non-silicone) and non-ionic solvent.

ionic oxirane containing silicone, non-ionic hydride silicone, and non-ionic oxirane compound (silicone or non-silicone) and non-ionic solvent.

Non-ionic oxirane containing silicone, ionic hydride silicone and non-ionic oxirane compound (silicone or non-silicone) and non-ionic solvent.

Ionic hydride silicone and non-ionic oxirane compound (silicone or non-silicone) and non-ionic solvent.

Non-ionic hydride silicone and non-ionic oxirane compound (silicone or non-silicone) and ionic solvent.

In one general embodiment herein, the amounts of the oxirane containing compound (silicone or non-silicone); the one or more silicon hydride activators; and, the effective amount of catalyst for ring-opening polymerization reaction of oxirane moiety are such that it is present in the personal care composition in the amounts indicated in the separate sections details below, but can be present in either ionic or non-ionic containing forms in the same amounts as detailed below, whether the below embodiments describe the component as containing or not containing ionic moieties.

In one general embodiment the solvent for swelling the crosslinked ionic silicone network is present in the personal care composition in an amount of from about 2 to about 98 weight percent, more specifically from about 5 to about 50 weight percent.

Oxirane Silicone Copolymer Bearing Ionic Radicals

In one embodiment herein the at least one oxirane silicone copolymer bearing ionic radicals has the general formula (IV):

$$M^2_a M^H_b M^E_c M^I_d D^2_e D^H_f D^E_g D^I_h T^2_i T^H_j T^E_k T^I_l Q_m. \quad \text{(IV)}$$

which is defined as described above and herein.

As used herein the terminology "hydrocarbon radical" includes acyclic hydrocarbon radicals, alicyclic hydrocarbon radicals and aromatic hydrocarbon radicals.

As used herein in reference to a hydrocarbon radical, the term "monovalent" means that the radical is capable of forming one covalent bond per radical, the term "divalent" means that the radical is capable of forming two covalent bonds per radical and the term "trivalent" means that the radical is capable of forming three covalent bonds per radical. Generally, a monovalent radical can be represented as having been derived from a saturated hydrocarbon compound by conceptual removal of one hydrogen atom from the compound, a divalent radical can be represented as having been derived from a saturated hydrocarbon compound by conceptual removal of two hydrogen atoms from the compound and a trivalent radical can be represented as having been derived from a saturated hydrocarbon compound by conceptual removal of three hydrogen atoms from the compound. For example, an ethyl radical, that is, a —CH$_2$CH$_3$ radical, is a monovalent radical; a dimethylene radical, that is, a —(CH$_2$)$_2$— radical, is a divalent radical and an ethanetriyl radical, that is,

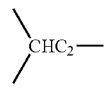

radical, is a trivalent radical, each of which can be represented as having been derived by conceptual removal of one or more hydrogen atoms from the saturated hydrocarbon ethane.

As used herein, the terminology "acyclic hydrocarbon radical" means a straight chain or branched hydrocarbon radical, preferably containing from 1 to 60 carbon atoms per radical, which may be saturated or unsaturated and which may be optionally substituted or interrupted with one or more atoms or functional groups, such as, for example, carboxyl, cyano, hydroxy, halo and oxy. As long as these functional groups do not interfere with the cationic cure mechanism of the epoxide or oxirane moiety, suitable monovalent acyclic hydrocarbon radicals may include, for example, alkyl, alkenyl, alkynyl, hydroxyalkyl, cyanoalkyl, carboxyalkyl, alkyloxy, oxaalkyl, alkylcarbonyloxaalkylene, carboxamide and haloalkyl, such as, for example, methyl, ethyl, sec-butyl, tert-butyl, octyl, decyl, dodecyl, cetyl, stearyl, ethenyl, propenyl, butynyl, hydroxypropyl, cyanoethyl, butoxy, 2,5,8-trioxadecanyl, carboxymethyl, chloromethyl and 3,3,3-fluoropropyl.

Suitable divalent acyclic hydrocarbon radicals include, for example, linear or branched alkylene radicals, such as, for example, methylene, dimethylene, trimethylene, decamethylene, ethylethylene, 2-methyltrimethylene, 2,2-dimethyltrimethylene and linear or branched oxalkylene radicals such as, for example, methyleneoxypropylene. Suitable trivalent acyclic hydrocarbon radicals include, for example, alkanetriyl radicals, such as, for example, 1,1,2-ethanetriyl, 1,2,4-butanetriyl, 1,2,8-octanetriyl, 1,2,4-cyclohexanetriyl and oxaalkanetriyl radicals such as, for example, 1,2,6-triyl-4-oxahexane.

As used herein the term "alkyl" means a saturated straight or branched monovalent hydrocarbon radical. In a preferred embodiment, monovalent alkyl groups are selected from linear or branched alkyl groups containing from 1 to 60 carbons per group, such as, for example, methyl, ethyl, propyl, iso-propyl, n-butyl, iso-butyl, sec-butyl, tert-butyl, pentyl, hexyl, heptyl, decyl, dodecyl.

As used herein the term "alkenyl" means a straight or branched monovalent terminally unsaturated hydrocarbon radical, preferably containing from 2 to 10 carbon atoms per radical, such as, for example, ethenyl, 2-propenyl, 3-butenyl, 5-hexenyl, 7-octenyl and ethenylphenyl.

As used herein, the terminology "alicyclic hydrocarbon radical" means a radical containing one or more saturated hydrocarbon rings, preferably containing from 4 to 12 carbon atoms per ring, per radical which may optionally be substituted on one or more of the rings with one or more alkyl radicals, each preferably containing from 2 to 6 carbon atoms per alkyl radical, halo radicals or other functional groups and which, in the case of a monovalent alicyclic hydrocarbon radical containing two or more rings, may be fused rings. Suitable monovalent alicyclic hydrocarbon radicals include, for example, cyclohexyl and cyclooctyl. Suitable divalent hydrocarbon radicals include, saturated or unsaturated divalent monocyclic hydrocarbon radicals, such as, for example, 1,4-cyclohexylene. Suitable trivalent alicyclic hydrocarbon radicals include, for example, cycloalkanetriyl radicals such as, for example, 1-dimethylene-2,4-cyclohexylene, 1-methylethylene-3-methyl-3,4-cyclohexylene.

As used herein, the terminology "aromatic hydrocarbon radical" means a hydrocarbon radical containing one or more aromatic rings per radical, which may, optionally, be substituted on the aromatic rings with one or more alkyl radicals, each preferably containing from 2 to 6 carbon atoms per alkyl radical, halo radicals or other functional groups and which, in the case of a monovalent aromatic hydrocarbon radical containing two or more rings, may be fused rings. Suitable monovalent aromatic hydrocarbon radicals include, for example, phenyl, tolyl, 2,4,6-trimethylphenyl, 1,2-isopropylmethylphenyl, 1-pentalenyl, naphthyl, anthryl, eugenol and allylphenol as well as aralkyl radicals such as, for example, 2-phenylethyl. Suitable divalent aromatic hydrocarbon radicals include, for example, divalent monocyclic arenes such as, for example, 1,2-phenylene, 1,4-phenylene, 4-methyl-1,2-phenylene, phenylmethylene. Suitable trivalent aromatic hydrocarbon radicals include, for example, trivalent monocyclic arenes such as, for example, 1-trimethylene-3,5-phenylene.

In one non-limiting embodiment herein, $R^{19}$, $R^{20}$, $R^{21}$, $R^{29}$, $R^{30}$ and $R^{34}$ are as defined herein.

Some specific non-limiting examples of hydrocarbon radicals as defined herein that may be suitable are methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl, cycloheptyl radicals and methylcyclohexyl radicals. Some specific non-limiting examples of aryl hydrocarbon radicals that may be suitable are phenyl, napthyl; m- and p-tolyl, xylyl, ethylphenyl and benzyl.

In another embodiment herein, $R^{23}$, $R^{24}$ and $R^{31}$ are as defined herein;

In yet another embodiment herein, $R^{25}$, $R^{26}$ and $R^{32}$ are as defined herein.

In yet another further embodiment herein, $R^{27}$, $R^{28}$ and $R^{33}$ are as defined herein In one specific embodiment herein, A is a divalent arylene group selected from the group consisting of:
—(CH$_2$)$_o$C$_6$H$_4$(CH$_2$)$_p$—,
—CH$_2$CH(CH$_3$)(CH$_2$)$_p$C$_6$H$_4$— and,
—CH$_2$CH(R$^1$)(CH$_2$)$_o$C$_6$H$_3$R"—
where R$^1$ is a monovalent hydrocarbon radical having from one to sixty carbon atoms, more specifically, from one to 30 carbon atoms, even more specifically from 1 to 12 carbon atoms and most specifically from 1 to 6 carbon atoms;
and
where o has a value of 0 to 20, more specifically from 1 to 10 and p has a value of 0 to 20, specifically from 0 to 10.

In another specific embodiment herein, A is a divalent alkylene group of the formula —(CHR$^{16}$)$_q$— where q has a value of from 1 to 20, specifically from 1 to about 10 and R$^{16}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms.

In yet another specific embodiment herein, A is selected from the group consisting of —CH$_2$CH$_2$CH$_2$—, —CH$_2$CH(CH$_3$)—, —CH$_2$CH(CH$_3$)CH$_2$—, and —CH$_2$CH$_2$CH(CH$_2$CH$_3$)CH$_2$CH$_2$CH$_2$—.

In yet even another specific embodiment herein A is of the formula:

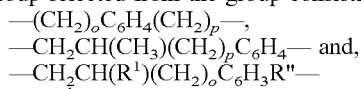
—(CHR$^{16}$)$_q$—O—CH(R$^{16}$)(CH$_2$)$_{q'}$—O—(CH$_2$)— wherein q has a value of from 0 to 50, more specifically from 3 to about 12 and q' has a value of from 1 to 50, more specifically from 2 to about 12 and R$^{16}$ is hydrogen or a monovalent hydrocarbon radical having from one to sixty carbon atoms, more specifically, from one to 30 carbon atoms, even more specifically from 1 to 12 carbon atoms and most specifically from 1 to 6 carbon atoms, optionally containing at least one heteroatom, such as the non-limiting examples of O, N, S or halogen.

In one embodiment herein, M can be a cation independently selected from univalent and polyvalent forms of Li, Na, K, Cs, Mg, Ca, Ba, Zn, Cu, Fe, Ni, Ga, Al, Mn, Cr, Ag, Au, Pt, Pd, Pb, Sb, Ru, Sn and Rh, such as the non-limiting examples of Mn$^{+2}$ and Mn$^{+3}$.

In one non-limiting embodiment herein M can specifically be a cation selected from univalent and polyvalent forms of Li, Na, K, Mg, Ca, Ba, Zn, Al, Ag, In another specific non-limiting embodiment herein the stoichiometric subscripts a', b', c', d', e', f', g', h', i', j', k', l' and m' are either zero or positive subject to the following limitations: c'+g'+k'>1, more specifically, c'+g'+k'>2; d'+h'+l'>1, more specifically d'+h'+l'>2; b'+f'+j'>c'+g'+k'; 3≥a'+b'+c'+d'+e'+f'+g'+h'+i'+j'+k'+l'+m'≤6000, more specifically 3≥a'+b'+c'+d'+e'+f'+g'+h'+i'+j'+k'+l'+m'≤4000 and most specifically, 3≥a'+b'+c'+d'+e'+f'+g'+h'+i'+j'+k'+l'+m'≤6000; and, b'+f'+j'>1, more specifically b'+f'+j'>2 if silicone hydride activator (iv) is absent.

In one embodiment herein the amount of oxirane silicone copolymer bearing ionic radicals is based on the total weight of the personal care composition which contains a crosslinked ionic silicone network which is formed by the polymerization of a silicone polymer containing oxirane moiety, silyl hydride moiety and ionic radicals. In one non-limiting embodiment, this amount is of from about 1 parts by weight to about 99 parts by weight, more specifically from about 5 parts by weight to 50 parts by weight, more specifically from about 10 parts by weight to about 40. Such amounts can be used as the amount of the ionically-modified crosslinked silicone network gel in the oil phase of the personal care composition.

It will be understood herein that the setting apart of the specification into portions such as oxirane, silicon-hydride, solvent, catalyst, personal care composition and processes thereto are only for means of ease to the reader and are not limiting in any aspect as to the various descriptive support provided in the respective sections, and such descriptive support applies equally and interchangeably to all portions of the specification. Thus, it is understood herein that the respective R definitions, subscript values and other variables defined herein with regard to one section, such as for example, the silicon-hydride can have the same definitions with regard to the description section relating to the oxirane functionalized silicone, the solvent and the catalyst, as well as the process embodiments herein, and also in any other way these variables have been described elsewhere in the composition or process embodiments described herein, and vice-versa.

Oxirane Ring-Opening Polymerization Catalyst

In one embodiment herein the oxirane ring-opening polymerization catalyst is an acid catalyst capable of polymerizing an epoxy group.

In a more specific embodiment, the acid catalyst capable of polymerizing an epoxy group is selected from onium salt generated acids; metal salts selected from the group consisting of aluminum trichloride and ferric chloride; lanthium triflates; and, platinum compounds.

In one even more specific embodiment, the acid catalyst is a lanthium triflate of the general formula:

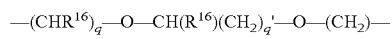
M(OSO$_2$CF$_3$)$_{n-z}$X$_z$ where M is the cation derived from a lanthanide and n is the valence of the lanthanide in the compound, X is an additional organic or inorganic salt residue (anionic residue), z is a number lower than n or 0.

The term "lanthanide" (M) shall be selected out of lanthanum and each of the chemical elements whose atomic number is between 58 (cerium) and 71 (lutetium), inclusive. In one specific embodiment, the lanthanide is selected from the group consisting of lanthan, ytterbium and samarium.

Some lanthanide triflates are commercial products or can be obtained by conventional, well-known methods. As X other organic and/or inorganic salt residues can be used, e.g., anions such as $Cl^-$, $Br^-$, $J^-$, $NO_3^-$, $HSO_4^-$, $H_2PO_3^-$, $HCO_3^-$, $CH_3COO^-$, $C_2H_5OO^-$, $C_6H_5COO^-$ which may form mixed salts with the lanthanide M.

Z is a number between 0 and n−1, so that at least one triflate residue is included in the lanthium triflate. More specifically the lanthium triflate is such that Z is 0 or 1, more specifically Z is 0. The lanthium triflate may comprise one or more metal ions M which may be the same or different.

In another embodiment herein the oxirane ring-opening polymerization-effective catalyst can be a platinum catalyst which operates under cationic cure conditions to ring-open the oxirane group of the oxirane silicone copolymer bearing ionic radicals. It will be understood herein that cationic polymerization conditions comprise any reaction parameters that provide for the ring-opening of the oxirane moiety with a silyl-hydride moiety.

Cationic polymerization conditions can be generated by addition of an acid catalyst capable of polymerizing an epoxy group such as, for example, by addition of onium salt generated acids and certain metal salts, such as, for example, aluminum trichloride and ferric chloride, which act as Lewis acids or by addition of lanthanide triflates, see PCT Int. Appl. WO 0008,087. Acid catalyzed polymerization of epoxides is a well known method of forming organic polymers and has been applied to epoxy-functional siloxane compounds in order to form siloxane polyalkyleneoxide block copolymers for use in a variety of applications as, for example, release coatings on paper, see, for example, U.S. Pat. No. 4,279,717, and in conjunction with organic materials to form coatings and modified plastic compositions, see for example, U.S. Pat. Nos. 5,354,796 and 5,663,752.

One precautionary note must be observed, that is if the cationic polymerization is conducted in the presence of cyclic siloxanes, e.g. $D_3$, $D_4$ or $D_5$ and the like, the strength of the acid catalysis employed must be such that cationic polymerization of the epoxide moiety occurs but polymerization of the cyclic siloxane does not occur to any appreciable extent.

Many types of platinum catalysts are known and such platinum catalysts may be used for the oxirane ring-opening polymerization reaction in the present instance. When optical clarity is required the preferred platinum catalysts are those platinum compound catalysts that are soluble in the reaction mixture. The platinum compound can be selected from those having the formula ($PtCl_2Olefin$) and $H(PtCl_3Olefin)$ as described in U.S. Pat. No. 3,159,601, hereby incorporated by reference. A further platinum containing material usable in the compositions of the present invention is the cyclopropane complex of platinum chloride described in U.S. Pat. No. 3,159,662 hereby incorporated by reference. Further the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference. The catalysts most specifically used herein are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in Advances in Organometallic Chemistry, volume 17, pages 407 through 447, F. G. A. Stone and R. West editors, published by the Academic Press (New York, 1979).

Other types of precious metal catalysts may also be used herein, such as the non-limiting examples of complexes of rhodium, ruthenium, palladium, osmium, iridium, and combinations thereof.

Persons skilled in the art can easily determine an effective amount of platinum catalyst. The oxirane ring-opening polymerization effective catalyst can be present in a very wide range, but normally a range of from between 0.01 and 7 parts per hundred parts resin (phr), more specifically from between 0.1 and 5 phr. In one embodiment herein the basis amount (i.e., the phr) of the acid catalyst capable of polymerizing an epoxy group is based on the amount of oxirane silicone copolymer bearing ionic radicals or the amounts of the respective components used to produce the oxirane silicone copolymer bearing ionic radicals.

Solvent

In one non-limiting embodiment herein, if the hydride-functional silicone and the oxirane-functionalized compound do not bear any ionic group, the solvent can comprise the ionic moieties present in the ionically-modified silicone cross-polymer network, wherein the reaction chemistry between the compounds present in the reaction mixture in the presence of the solvent results in the solvent being physically entrained within the crosslinked ionic silicone network.

In one non-limiting embodiment herein the solvent comprises an ionically-modified silicone polymer having the general structure (V) as described herein:

$$M^3{}_{\alpha'}M^4{}_{\beta'}D^3{}_{\chi'}D^4{}_{\delta'}T^3{}_{\epsilon'}T^4{}_{\phi'}Q_{\gamma'} \qquad (V)$$

and the subscripts α', β', χ', δ', ε', φ', and γ' are zero or positive subject to the following limitations: $2 \leq \alpha' + \beta' + \chi' + \delta' + \epsilon' + \phi' + \gamma' \leq 6000$ and, $\beta' + \delta' + \phi' > 0$.

Solvents suitable for use as the carrier solvent herein are those compounds or mixtures of two or more compounds that are in a liquid state at or near room temperature, e.g., 20° C. to about 50° C. and about one atmosphere pressure, and include such non-limiting examples as those selected from silicone fluids, hydrocarbon fluids, esters, alcohols, fatty alcohols, glycols, organic waxes and organic oils.

In one embodiment, the fluid component of the present invention comprises an emollient compound. Suitable emollient compound include any fluid that provides emollient properties, that is, that when applied to skin, tend to remain on the surface of the skin or in the stratum corneum layer of the skin to act as lubricants, reduce flaking and to improve the appearance of the skin. Emollient compound are generically known and include, for example, hydrocarbons, such as for example, isododecane, isohexadecane and hydrogenated polyisobutene, organic waxes, such as for example, jojoba, silicone fluids, such as, for example, cyclopentasiloxane, dimethicone and bis-phenylpropyl dimethicone, esters, such as, for example, octyldodecyl neopentanoate and oleyl oleate, as well as fatty acids and alcohols, such as for example, oleyl alcohol and isomyristyl alcohol.

In one specific embodiment the carrier solvent is at least one selected from the group consisting of isodecane, isohexadecane, hydrogenated polyisobutene, jojoba, cylcopentasiloxane, dimethicone, bis-phenylpropyl dimethicone, octyldodecyl neopentanoate, oleyl oleate, oleyl alcohol and isomyristyl alcohol.

In another embodiment the carrier solvent is a cyclic silicone fluid of the general formula $D_r$, where $D=R^{10}R^{11}SiO_{2/2}$ and where $R^{10}$ and $R^{11}$ are monovalent hydrocarbon radicals of from 3 to 6 carbon atoms, more specifically methyl, and r is an integer of from 3 to 12, more specifically, from 4 to 6. Specifically, the cyclic silicone fluid can be selected from hexamethylcyclotrisiloxane, octamethylcyclotetrasiloxane, decamethylcyclopentasiloxane and dodecamethylcyclohexasiloxane.

In one specific embodiment, the carrier solvent is a silicone fluid which is a linear or branched organopolysiloxane having the general formula:

$$M'D'_sT'_tM'$$

where
$M'=R^{23}_3SiO_{1/2}$;
$D'=R^{24}_2SiO_{2/2}$; and,
$T'=R^{25}SiO_{3/2}$,
wherein $R^{23}$, $R^{24}$ and $R^{25}$ are each independently alkyl, aryl or aralkyl containing up to 60 carbon atoms, more specifically containing from one to 30 carbon atoms, even more specifically containing from 1 to 12 carbon atoms and most specifically from 1 to 6 carbon atoms, such as methyl;

the subscripts s and t are each independently integers from 0 to 300, specifically from 0 to 50 and most specifically from 0 to 20.

In one non-limiting embodiment herein the crosslinked ionic silicone network is swellable by the carrier solvent.

In another embodiment herein the carrier solvent is a hydrophilic emollient selected from the group consisting of glycerine, sorbitol, aqueous solution of moisturizing additives and combinations thereof.

In one specific embodiment the carrier solvent is selected from a silicone oil, an organic oil and combinations thereof.

Because it is possible to vary the compositional parameters of the crosslinked ionic silicone network of the invention in an almost limitless fashion, by varying the compositional parameters of the oxirane silicone copolymer bearing ionic radicals, some compositions herein are both water swellable and oil swellable while others are only water swellable or oil swellable, and some compositions herein will not be swellable with any of the solvents discussed herein. The amount of crosslinking present in the crosslinked ionic silicone network may be characterized with respect to the degree of swelling exhibited by the network in the carrier solvent. In another embodiment, the crosslinked structure of the crosslinked ionic silicone network is effective to allow the crosslinked ionic silicone network to be swollen from its original volume to a swollen volume that is a factor of from 1.01 to 5000, more preferably from 2 to 1000, and even more preferably from 5 to 500, times its original volume. The original volume of the crosslinked ionic silicone network can be determined, for example, by extracting or evaporating all of the carrier solvent component from the personal care composition of the present invention to leave the original volume, that is, the volume of the crosslinked ionic silicone network in the absence of the fluid.

In a preferred embodiment, the personal care composition of the present invention comprises, per 100 parts by weight ("pbw") of the crosslinked ionic silicone network, from 1 pbw to 99.9 pbw, more preferably from 70 pbw to 99.5 pbw, and still more preferably from 85 pbw to 99 pbw of the carrier solvent.

Silicon-Hydride Activator

In one embodiment herein the at least one hydride-functional silicone has the general formula (VI):

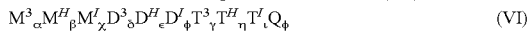

as described herein.

Silicon hydride activator that is used herein is such that it is suitable for ring opening the oxirane moiety of the oxirane silicone copolymer bearing ionic radicals in order to provide for the crosslinking present in the resultant crosslinked ionic silicone network. It includes any silicon compound derived from at least two organosiloxane units and having terminal and/or pendant Si—H groups. In one embodiment herein the silicon-hydride activator is such that it contains at least some Si—H functional units along its polymer backbone. It may or may not in addition to these internal Si—H functional units also contain terminal Si—H functional units.

The Si—H functional silicon compound is capable of reacting with the olefinic moieties of the above-mentioned oxirane moieties via addition reaction. Examples of suitable Si—H functional silicon compounds include 1,1,3,3-tetraalkyldisiloxane, dialkylhydrogensiloxy-endstopped polydialkylsiloxane, polydialkylalkylhydrogen-siloxane copolymer, and trialkylsiloxy-endstopped polydialkyl-alkylhydrogensiloxane copolymer comprising at least two alkylhydrogen siloxy groups. Other examples of Si—H containing silicon compounds include 1,1,3,3-tetramethyldisiloxane, 2,4,6,8-tetramethylcyclotetrasiloxane, methyldimethoxysilane, triethylsilane, and methyldiethoxysilane. The preferred silicon hydride activator used in the present invention is 1,1,3,3-tetramethyldisiloxane.

Although the silicon-hydride activator may be a silane, it is most advantageous to use an Si—H functional polysiloxane linear polymer. Thus, one embodiment of the present invention utilizes an Si—H functional linear polysiloxane polymer represented by the formula:

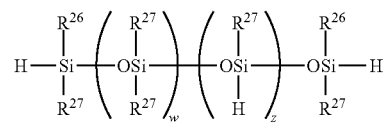

wherein $R^{26}$ and $R^{27}$ are each independently a monovalent hydrocarbon radical of from 1 to about 60 carbon atoms, specifically from 1 to about 20 carbon atoms and more specifically from 1 to about 8 carbon atoms, and in some embodiment, the aforestated ranges can have lower limits of 2 or 3 carbon atoms;

"w" is from 0 to about 1,000; and "z" is from about 0 to about 200. More preferably, "w" varies from about 10 to about 500 and "z" varies from about 5 to about 200. The lower endpoint of "w" and "z" can in one non-limiting embodiment also be any one of 1, 2, 3 or 4.

Another embodiment of the present invention utilizes cyclic silicone hydrides as the silicon-hydride activator. Such cyclic silicone hydrides are well known in the art and may be represented by the formula:

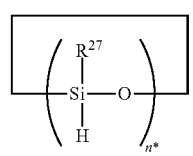

wherein $R^{27}$ is as defined above and "n*" is from about 3 to about 12, specifically from about 4 to about 10.

In one non-limiting embodiment, the amount of silicon hydride activator present in the personal care composition is from about 0.01 pbw to about 10 pbw, more specifically from about 0.05 pbw to about 7 pbw and most specifically from about 0.1 pbw to about 5 pbw based on 100 parts by weight of the oxirane silicone copolymer bearing ionic radicals.

Personal Care Composition

In one embodiment herein, the compositions of the present invention are self-emulsifying.

In another embodiment herein, the personal care composition may be further processed under low to high shear to adjust the viscosity and sensory feel of the composition. This may be achieved, for example, by subjecting the composition to a moderate to high shearing force. High shear may be applied using, for example, a Sonolator apparatus, a Gaulin Homogenizer or a Micro Fluidizer apparatus. Optionally, one or more carrier solvent may be added to the silicone composition prior to the shearing.

In a specific embodiment, the personal care composition of the present invention is a solid, typically having a creamy consistency, wherein the crosslinked ionic silicone network acts as a means for gelling the fluid to reversibly impart characteristics of a solid to the fluid. At rest, the personal care composition exhibits the properties of a solid gel material. The personal care composition of the present invention exhibits high stability and resistance to syneresis, that is, the composition exhibits little or no tendency for fluid to flow from the composition and imparts high stability and syneresis resistance to personal care compositions which include the crosslinked ionic silicone network as a component. The high stability and syneresis resistance persists with prolonged aging of such crosslinked ionic silicone networks and personal care compositions. However, carrier solvent may be released from the crosslinked ionic silicone network by subjecting the personal care composition to a shearing force, such as, for example, by rubbing the composition between one's fingers, to provide improved sensory feel characteristic of the fluid component of the silicone material.

Water (or a water equivalent such as a non-aqueous hydroxylic solvent), siloxane, linear or cyclic, or lipophilic fluid (oil swelling agent, oil swellable) may be used as the carrier solvent which may function as a swelling agent. Lipophilic fluids suitable for use as the carrier solvent component of the composition of the present invention are those described herein. In a preferred embodiment, the carrier solvent component of the composition of the present invention exhibits a viscosity of below about 1,000 cSt, preferably below about 500 cSt, more preferably below about 250 cSt, and most preferably below 100 cSt, at 25° C.

In one preferred embodiment, the network is a crosslinked ionic silicone network that is insoluble in various fluid components, but that is capable of being swollen by the carrier solvent. The amount of crosslinking present in the crosslinked ionic silicone network may be characterized with respect to the degree of swelling exhibited by the network in the carrier solvent.

In another preferred embodiment, the crosslinked structure of the crosslinked ionic silicone network is effective to allow the network to be swollen by a low molecular weight silicone fluid, such as, for example, decamethylcyclopentasiloxane, from its original volume to a swollen volume as stated above.

The crosslinked ionic silicone network of the present invention may be utilized as prepared or as the silicone component in personal care emulsions. As is generally known, emulsions comprise at least two immiscible phases one of which is continuous and the other which is discontinuous. In one embodiment herein, the non-miscible phases (immiscible phases) can be selected from the group consisting of aqueous, non-aqueous, and solid particulates.

Further emulsions may be liquids with varying viscosities or solids. Additionally, the particle size of the emulsions may render them microemulsions, and when sufficiently small, microemulsions may be transparent. Further it is also possible to prepare emulsions of emulsions and these are generally known as multiple emulsions. These emulsions may be: 1) aqueous emulsions where the discontinuous phase comprises water and the continuous phase comprises the crosslinked ionic silicone network of the present invention; 2) aqueous emulsions where the discontinuous phase comprises the crosslinked ionic silicone network of the present invention and the continuous phase comprises water; 3) non-aqueous emulsions where the discontinuous phase comprises a non-aqueous hydroxylic solvent and the continuous phase comprises the crosslinked ionic silicone network of the present invention; and 4) non-aqueous emulsions where the continuous phase comprises a non-aqueous hydroxylic organic solvent and the discontinuous phase comprises the crosslinked ionic silicone network of the present invention.

In one embodiment herein, the crosslinked ionic silicone network is compatible with a cosmetic additive, which can be either hydrophobic or hydrophilic. In one embodiment herein, the crosslinked ionic silicone network herein is compatible with hydrophilic materials, e.g., hydrophilic cosmetic materials. In one embodiment, the crosslinked ionic silicone network is compatible with a particulate additive e.g., a hydrophilic particulate additive, e.g, silica, titania and boron nitride. In another more specific embodiment, the particulate additive is selected from inorganic particulates, polymeric latexes, and pigments. In another embodiment the hydrophilic personal care ingredients with which the crosslinked ionic silicone network is compatible can be antiperspirant ingredients, anti-aging ingredients, skin-calming ingredients and/or moisturizing ingredients. Some such ingredients are those employed in hand, body and face lotions and creams, sunscreen products, antiperspirants and hair colors, such as the non-limiting examples of solvents, buffers, bleaches, waving agents, astringents, stabilizers, deodorants and antiperspirants. It is likewise now possible to provide hydrophilic skin moisturizers such as glycerol in anhydrous formulas, such as e.g. in lip products, glycerol, or other active materials.

As used herein the term "non-aqueous hydroxylic organic compound" or "non-aqueous hydroxylic solvent" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile siloxanes. It is capable of being blended into personal care formulations for hair care, skin care, and the like. In one embodiment herein, the crosslinked ionic silicone network can bind and slow release cosmetic actives.

In one embodiment the personal care formulation can be a personal care application selected from the group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nail creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a more specific embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the crosslinked ionic silicone networks. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions; such as is described above.

In one useful embodiment, an antiperspirant composition comprises the crosslinked ionic silicone networks of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the crosslinked ionic silicone network, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the crosslinked ionic silicone network, and a coloring agent, such as, for example, a pigment, a water soluble dye or a liposoluble dye.

In another useful embodiment, the compositions of the present invention are utilized in conjunction with fragrant materials. These fragrant materials may be fragrant compounds, encapsulated fragrant compounds or fragrance releasing compounds that either the neat compounds or are encapsulated.

Process of Preparing Personal Care Composition Containing Crosslinked Ionic Silicone Network Gel As stated above, there is provided herein a process of preparing a personal care composition comprising an oil phase and an aqueous phase which process comprises adding a crosslinked ionic silicone network gel to the oil phase of a personal care composition wherein the crosslinked ionic silicone network gel is made by:
a) polymerizing:
   i. an oxirane-functionalized compound (silicone or non-silicone),
   ii. an oxirane ring-opening polymerization catalyst,
   iii. a carrier solvent; and,
   iv. optionally, one or more silicon hydride activators; subject to the limitation that at least (i), (iii) or (iv) comprises the ionically modified silicone of general formula (I).

$$M^1{}_a M^2{}_b M^3{}_c D^1{}_d D^2{}_e D^3{}_f T^1{}_g T^2{}_h T^3{}_i Q_j \qquad (I)$$

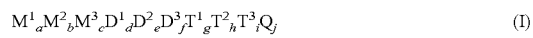

as described herein, by epoxy ring-opening polymerization with hydride moiety to form a crosslinked ionic silicone network; and,
b) shearing the crosslinked ionic silicone network during and/or after the polymerization step with at least one carrier solvent (iii) to form the crosslinked ionic silicone network gel.

In another embodiment, there is provided herein a process of preparing a personal care composition comprising an oil phase and an aqueous phase which personal care composition is made by the process of adding at least one crosslinked ionic silicone network gel to the oil phase of a personal care composition wherein the crosslinked ionic silicone network gel is made by:
(a) reacting a molecule having the general formula (Ia):

$$M_a M^H{}_b M^I{}_d D_e D^H{}_f D^I{}_h T_i T^H{}_j T^I{}_l Q_m \qquad (Ia)$$

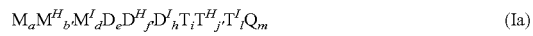

wherein:

$M^3 = R^{35}R^{36}R^{37}SiO_{1/2}$
$M^H = R^{38}R^{39}HSiO_{1/2}$
$M^I = R^{40}R^{41}R^ISiO_{1/2}$
$D^3 = R^{42}R^{43}SiO_{2/2}$
$D^H = R^{44}HSiO_{2/2}$
$D^I = R^{45}R^ISiO_{2/2}$
$T^3 = R^{46}SiO_{3/2}$
$T^H = HSiO_{3/2}$
$T^I = R^ISiO_{3/2}$
$Q = SiO_{4/2}$; and where $R^{35}$, $R^{36}$, $R^{37}$, $R^{42}$, $R^{43}$ and $R^{46}$ are independently monovalent hydrocarbon radicals having from one to sixty carbon atoms, more specifically from 1 to about 20 carbon atoms and most specifically from 1 to about 8 carbon atoms;

$R^{38}$, $R^{39}$ and $R^{44}$ are independently hydrogen or monovalent hydrocarbon radicals having from one to sixty carbon atoms, more specifically from 1 to about 20 carbon atoms and most specifically from 1 to about 8 carbon atoms;

$R^{40}$, $R^{41}$ and $R^{45}$ are independently $R^I$ or monovalent hydrocarbon radicals having from one to sixty carbon atoms, more specifically from 1 to about 20 carbon atoms and most specifically from 1 to about 8 carbon atoms, where $R^I$ is a monovalent or multivalent radical bearing ionic group(s), and where the stoichiometric subscripts a, b', d, e, f', h, i, j', l and m are either zero or positive subject to the following limitations: $2 \geq a+b'+d+e+f'+h, +i+j'+l+m \leq 6000$, more specifically $2 \geq a+b'+d+e+f'+h, +i+j'+l+m \leq 4000$ and most specifically $2 \geq a+b'+d+e+f'+h, +i+j'+l+m \leq 2000$ and in some embodiments the aforestated ranges of $a+b'+d+e+f'+h,+i+j'+l+m$ can have lower limits of any one of 3, 4, 5, 10, 12, 18, 20, 30 and 50 as well as 100, 200, 300 and 500; $b+f+j>0$, more specifically, $b+f+j>1$, even more specifically, $b+f+j>2$ and yet more specifically $b+f+j$ is from 1 to about 100, further more specifically from 1 to about 50 and most specifically from 1 to about 10, wherein the stated ranges for $b+f+j$ can in some embodiments have lower endpoints of any one of 2, 3, 4, 5, 10, 50 or 100; and $d+h+l \geq 0$ more specifically, $d+h+l \geq 1$, even more specifically, $d+h+l \geq 2$ and yet more specifically $d+h+l$ is from 1 to about 100, further more specifically from 1 to about 50 and most specifically from 1 to about 10, wherein the stated ranges for $d+h+l$ can in some embodiments have lower endpoints of any one of 2, 3, 4, 5, 10, 50 or 100;

with an olefinically unsaturated molecule containing one or more oxirane moieties, and polymerizing of the reaction product of step (a) by epoxy ring-opening polymerization with the hydride moiety in the presence of an oxirane ring-opening polymerization catalyst, a carrier solvent, and, optionally a silyl-hydride molecule to produce the crosslinked ionic silicone network, provided, wherein the silyl-hydride molecule is absent, the molar amount of olefinic unsaturated moiety in the olefinically unsaturated molecule containing one or more oxirane moieties of step (a) is less than the molar amount of silyl hydride moiety in general formula (Ia); and, (b) shearing the reaction product of step (a) in the presence of at least one carrier solvent (iii) to provide the crosslinked ionic silicone network gel.

It will be understood herein that the respective R values, subscripts and other variables defined herein can have the same definitions in the process embodiments herein as these variables have in the composition embodiments described herein. In one embodiment the subscripts b', f' and j' can have the same definitions as subscripts b, f and j have elsewhere herein.

In one embodiment herein that the reaction of a molecule of formula (V) with an olefinically unsaturated molecule containing one or more oxirane moieties can be conducted under general hydrosilylation conditions which can comprises the use of a precious metal catalyst such as those described herein, e.g., a platinum catalyst, and in conditions as described herein and known to those skilled in the art.

As used herein the phrase "an olefinically unsaturated molecule containing one or more oxirane moieties" means a molecule possessing one or more interior, pendant or terminal carbon carbon double bonds simultaneously with one or more interior, pendant or terminal three membered oxygen containing heterocyclic rings (chemically the phrase "three membered oxygen containing heterocyclic ring" is used herein interchangeably with the oxirane or epoxide structures). The simplest chemical structure exemplified by such a definition is:

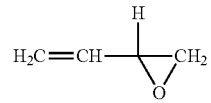

but also includes alicyclic structures exemplified by:

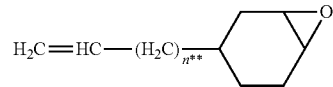

where the subscript n** may be zero or a positive integer, more preferably a positive integer ranging generally from 0 to about 10. It should be noted that both exemplified structures are terminal in both the olefinic moiety and the oxirane (epoxide) moiety. A more general chemical structure is wherein the olefinically unsaturated molecule containing one or more oxirane moieties is of the general formula (Ib):

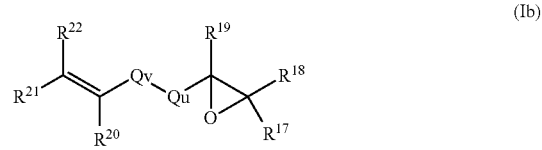

(Ib)

where $R^{17}$, $R^{18}$, $R^{19}$, $R^{20}$, $R^{21}$ and $R^{22}$ are each independently selected from the group of hydrogen and monovalent hydrocarbon radicals containing from 1 to 60 carbon atoms, $Q_u$ is a divalent or trivalent hydrocarbon radical containing from 1 to 60 carbon atoms, $Q_v$ is a divalent hydrocarbon radical containing from 1 to 60 carbon atoms and the subscripts u and v are independently zero or one, subject to the limitation that when $Q_u$ is trivalent, $R^{18}$ is hydrogen, and a carbon atom of $Q_u$ forms a bond with a carbon atom of $R^{17}$ and where $R^{20}$ and $R^{22}$ may be cis or trans to each other.

It is to be noted that acetylene analogs of the olefinically unsaturated oxirane containing molecules will produce similar species that will react to form similar products. Thus as used herein the phrase an olefinically unsaturated molecule containing one or more oxirane moieties is intended to also include an acetylenically unsaturated molecule containing one or more oxirane moieties. The phrase "an acetylenically unsaturated molecule containing one or more oxirane moieties" means a molecule possessing one or more interior, pendant or terminal carbon carbon triple bonds simultaneously with one or more interior, pendant or terminal three membered oxygen containing heterocyclic rings (chemically the phrase "three membered oxygen containing heterocyclic ring" is used herein interchangeably with the oxirane or epoxide structures).

When the olefinically unsaturated oxirane containing molecule is an olefinic epoxide, a specific example being formula (Ib) as described above, then $R^E$ as a substituent, becomes

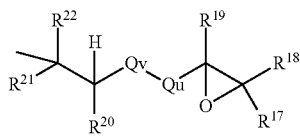

with all the definitions consistent with those as previously defined. When the epoxide is an acetylenic epoxide, a specific example being:

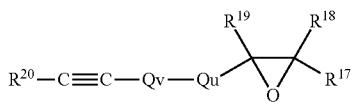

then $R^E$ as a substituent, becomes either:

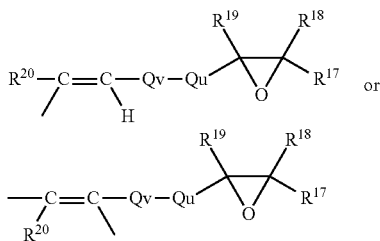

with all the definitions consistent with those as previously defined.

The olefinically unsaturated oxirane containing molecules are prepared in the normal manner through the use of a hydrosilylation reaction to attach a vinyl or allyl substituted epoxide onto an SiH bearing siloxane. SiH containing siloxanes are well known in the art and can be linear, branched, or cyclic in structure. Examples of useful vinyl or allyl substituted epoxides include 4-vinyl cyclohexene oxide, allyl glycidyl ether, limonene oxide, 1,2-epoxy-5-hexene, 1,2-epoxy-7-octene, norbornadiene monoepoxide and 1,2-epoxy-9-decene. Precious metal catalysts for making the olefinically unsaturated oxirane containing molecules are also well known in the art and comprise complexes of one or more of rhodium, ruthenium, palladium, osmium, iridium and platinum.

The reaction product of step (a) can in one embodiment be reacted under cationic polymerization conditions in the presence of an oxirane ring-opening polymerization-effective catalyst which is the same catalyst described herein, a carrier solvent as described herein, and, optionally a silyl-hydride molecule which is the silyl-hydride activator molecule described herein, to produce the crosslinked ionic silicone network, There is provided in another embodiment herein a process of preparing a crosslinked ionic silicone network for personal care applications comprising reacting a silicon hydride with a silicone which contains an oxirane moiety and an ionic radical moiety which silicone is of the general formula (Ic), which is as defined above and herein, in the presence of a hydrosilylation catalyst, e.g., a precious metal catalyst, to produce a crosslinked ionic silicone network.

In a specific embodiment herein the silicon hydride of such a process is of the general formula (Id):

$$M_a M^H{}_b D_e D^H{}_f T_i T^H{}_j Q_m. \quad (Id)$$

which is as defined herein. It will be understood herein that the respective R values, subscripts and other variables of the formula (Id) herein can have the same definitions in the process embodiments herein as these variables have in the composition embodiments described herein. The silicon hydride of the formula (Id) can be made by a variety of techniques that are known in the art, such as those described in U.S. Pat. No. 8,697,829, the contents of which are incorporated by reference herein.

EXAMPLES

Experimental Synthesis of Ionic Polyether Siloxane Copolymer Network Compositions Synthetic Example 1

99.02 g of a hydride fluid with approximate composition $M^H D_{300} D^*{}_2 D^H{}_4 M^H$ (where D* denotes the divalent siloxane unit bearing a sulfonate group; $M^H$ and $D^H$ each contain one silyl-hydride moiety and all the other silyl valences in the molecule are satisfied with methyl) was mixed with 1.1 g of vinyl cyclohexene oxide, 300 g of decamethyl cyclopentasiloxane (D5), and 0.1 g of a platinum divinyltetramethyldisiloxane catalyst solution. The result was heated to 90° C. After a couple of hours, an additional portion of platinum catalyst solution was added. The material was heated for a total of 4 hours at 80° C. In this way a gel material was obtained with a solids content of about 28%. Then, 500 g of additional D5 and 50 g of water were added and homogenized. The final gel had a solids content of about 8%. This material gave a very silky feel when rubbed on the skin.

Synthetic Example 2

99.02 g of a hydride fluid with approximate composition $M^H D_{300} D^I{}_2 D^H{}_4 M^H$ (where $M^H$ and $D^H$ are as defined above, and where $D^I$ denotes the divalent siloxane unit bearing a —CH$_2$CH(CH$_3$)C$_6$H$_4$SO$_3$Na unit and all other substituent in the silicone formula are methyl) was mixed with 1.1 g of vinyl cyclohexene oxide, 300 g of Isododecane (IDD), and 0.1 g of a platinum divinyltetramethyldisiloxane catalyst solution. The result was heated to 90° C. After a couple of hours, an additional portion of platinum catalyst solution was added. The material was heated for a total of 4 hours at 80° C. Then, 50 g of water was added and continued to stir for 1 hour. In this way a gel material was obtained which had a solids content of about 24%. This material gave a very silky feel when rubbed on the skin.

Synthetic Example 3

61.8 g of a hydride fluid with approximate composition $M^H D_{300} D^I{}_2 D^H{}_4 M^H$ (where $M^H$ and $D^H$ are as defined above and $D^I$ denotes a divalent siloxane unit bearing a CH$_2$CH(CH$_3$)C$_6$H$_4$SO$_3$Na moiety and all other substituents groups on the silicone formula are methyl) was mixed with 0.83 g of vinyl cyclohexene oxide, 154.7 g of Silsoft® 034, 4.49 g of Gulftene C30+ Alpha olefin from Chevron and 0.1 g of a platinum divinyltetramethyldisiloxane catalyst solution. The result was heated to 90° C. After 6 hours 1.0 g of a hydride cross-linker (vern 730) available from Momentive was added continued to stir at 90° C. for an hour. To the mixture, 0.5 g of 1-octene and 16 g of Silsoft® 034 were added and continued to stir for additional 2 h. In this way a gel material was obtained which had a solids content of about 25%. This material gave a very silky feel when rubbed on the skin.

Synthetic Example 4

55.9 g of a hydride fluid with approximate composition $M^HD_{150}D^I{}_2D^H{}_{2.2}M^H$ (where $M^H$ and $D^H$ are as defined above and $D^I$ denotes a divalent siloxane unit bearing a —CH$_2$CH(CH$_3$)C$_6$H$_4$SO$_3$Na moiety and all other substituents groups on the silicone formula are methyl) was mixed with 1.44 g of vinyl cyclohexene oxide, 135.4 g of Silsoft® 034, 3.58 g of Gulftene C30+ Alpha from Chevron and 0.06 g of a platinum divinyltetramethyldisiloxane catalyst solution. The result was heated to 90° C. After 6 hours 2.1 g of a hydride cross-linker (vern 730) from Momentive was added continued to stir at 90° C. for an hour. To the mixture, 0.88 g of 1-octene and 18 g of Silsoft® 034 were added and continued to stir for additional 2 h. In this way a gel material was obtained which had a solids content of about 27%. This material gave a very silky feel when rubbed on the skin.

Synthetic Example 5

300 g of a hydride fluid with approximate composition $M^HD_{133}D^H{}_{2.5}M^H$ ($M^H$ and $D^H$ are as defined above and all other moieties on the silicone formula are methyl) was mixed with 300 g of a sodium salt of sulfonic acid capped polydimethylsiloxane with an average D-length of 400, 8.45 g of vinyl cyclohexene oxide, 22.2 g of Gulftene C30+ Alpha Olefin Fraction from Chevron, 796 g of PDMS-5 (Momentive), and 0.1 g of a platinum divinyltetramethyldisiloxane catalyst solution. The result was heated to 80° C. for 6 hours. The resulting mixture was then swollen with a mixture of 938 g of additional PDMS-5 (Momentive) and homogenized to a soft gel.

Synthetic Example 6

300 g of a hydride fluid with approximate composition $M^HD_{133}D^H{}_{2.5}M^H$ ($M^H$ and $D^H$ are as defined above and all other moieties on the silicone formula are methyl) was mixed with 300 g of a phosphonic acid capped polydimethylsiloxane with an average D-length of 400, 8.45 g of vinyl cyclohexene oxide, 22.2 g of Gulftene C30+ Alpha Olefin Fraction from Chevron, 796 g of PDMS-5 (Momentive), and 0.1 g of a platinum divinyltetramethyldisiloxane catalyst solution. The result was heated to 80° C. for 6 hours. The resulting mixture was then swollen with a mixture of 938 g of additional PDMS-5 (Momentive) and homogenized to a soft gel.

Synthetic Example 7

300 g of a hydride fluid with approximate composition $M^HD_{133}D^H{}_{2.5}M^H$ ($M^H$ and $D^H$ are as defined above and all other moieties on the silicone formula are methyl) was mixed with 300 g of a carboxylic acid capped polydimethylsiloxane with an average D-length of 400, 8.45 g of vinyl cyclohexene oxide, 22.2 g of Gulftene C30+ Alpha Olefin Fraction from Chevron, 796 g of PDMS-5 (Momentive), and 0.1 g of a platinum divinyltetramethyldisiloxane catalyst solution. The result was heated to 80° C. for 6 hours. The resulting mixture was then swollen with a mixture of 938 g of additional PDMS-5 (Momentive) and homogenized to a soft gel.

Formulation Examples CF1-F12

| Ingredient | CF1 | CF2 | CF3 | F1 | F2 | F3 | F4 | F5 | F6 | F7 | F8 | F9 | F10 | F11 | F12 |
|---|---|---|---|---|---|---|---|---|---|---|---|---|---|---|---|
| Synthetic Example 1 | | | | 35 | | | | | | | | | | | |
| Synthetic Example 2 | | | | | 71 | | | | | | | | | | |
| Synthetic Example 3 | | | | | | 3.8 | 3.9 | | | 4.2 | | | | | |
| Synthetic Example 4 | | | | | | | | 4.2 | 4.2 | | 4.2 | 4.2 | 4.2 | 4.2 | 4.2 |
| Velvesil Plus (Momentive Performance Materials Pvt. Ltd.) | 35 | 71 | | | | | | | | | | | | | |
| Velvesil 034 (Momentive Performance Materials Pvt. Ltd.) | | | 6.3 | | | | | | | | | | | | |
| SF 1202 (Momentive Performance Materials Pvt. Ltd.) | | | 24 | | | | | | | | | | | | |
| Silsoft 034 (Momentive Performance Materials Pvt. Ltd) | | | | | 15.9 | 25 | 14.3 | | 14.3 | 14.3 | 14.3 | 14.3 | 14.3 | 14.3 | 13.6 |

-continued

| Ingredient | CF1 | CF2 | CF3 | F1 | F2 | F3 | F4 | F5 | F6 | F7 | F8 | F9 | F10 | F11 | F12 |
|---|---|---|---|---|---|---|---|---|---|---|---|---|---|---|---|
| SF 1540 (Momentive Performance Materials Pvt. Ltd) | | | 2.5 | | | 2 | 2.4 | 2.5 | 2.6 | 2.5 | 2.5 | 2.5 | 2.5 | 2.5 | 2.5 |
| 1% Brine | | | 65.1 | | | 78.2 | 66.6 | 76.9 | 72.7 | 76.9 | 76.9 | 77 | 76.9 | 76.9 | 73.7 |
| Glycerin | 65 | 14 | | 65 | 14 | | | | | | | | | | |
| Castor Oil | | 15 | | | 15 | | | | | | | | | | |
| TiO2-MT100 TV (Pigment) Tri-K Industries | | | | | | | 2 | 2.1 | 6.2 | | | | | | |
| Cloisite 30B (Southern Clay Products) | | | 2.2 | | | | | | | 2.1 | 2.1 | | | | |
| Niacinamide, Sigma Aldrich Ltd. | | | | | | | | | | | | 2 | | | |
| Tospearl (Momentive Performance Materials Pvt. Ltd) | | | | | | | | | | | | | 2.1 | | |
| Sisoft-E-Pearl (Momentive Performance Materials Pvt. Ltd) | | | | | | | | | | | | | | 2.14 | |
| Octylmethoxy-cinnamate | | | | | | | | | | | | | | | 6 |
| Compatibility | N | N | N | Y | Y | Y | Y | Y | Y | Y | Y | Y | Y | Y | Y |

Formulation Examples F13-F16

| Ingredient | CF4 | CF5 | CF6 | CF6 | F13 | F14 | F15 | F16 |
|---|---|---|---|---|---|---|---|---|
| Synthetic Example 2 | | | | | | | 35 | 71 |
| Synthetic Example 5 | | | | | 40 | | | |
| Synthetic Example 6 | | | | | | | | |
| Synthetic Example 7 | | | | | | 50 | | |
| Velvesil Plus (Momentive Performance Materials Pvt. Ltd.) | | | 35 | 71 | | | | |
| Velvesil DM (Momentive Performance Materials Pvt. Ltd) | 50 | 40 | | | | | | |
| Element-14 (Momentive Performance Materials Pvt. Ltd. | 40 | 40 | | | 40 | 40 | | |
| Glycerin | | 20 | 65 | 14 | 20 | | 65 | 14 |
| TiO2-MT100 TV (Pigment) Tri-K Industries | 10 | | | | 10 | | | |
| Castor Oil | | | | 15 | | | | 15 |
| Compatibility | N | N | N | N | Y | Y | Y | Y |

The compatibility of each formulation was evaluated under the accelerated aging conditions where each formulation was aged at 50° C. in a closed container for 8 weeks. Then each formulation was centrifuged at 2500 rpm for 15 minutes and compatibility of the formulation was then determined based on the visual was observation of phase separation. A non-compatible formulation has shown phase separation during the centrifugal test. The compatibility of formations was further confirmed by Hegman Test as well as Optical Microscope Analsysis. FIG. 1 herein shows the optical microscope images of examples CF3 and F5.

The above noted examples clearly demonstrate that all of the ionic silicone based compositions have shown significant improvement over traditional non-ionic silicone based composition with respect to the compatibility with hydrophilic and lipophilic ingredients, pigment dispersion and sensory feeling.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:
1. A process of preparing a personal care composition comprising at least an oil phase, wherein the process comprising
   a) reacting a silicone hydride with a sulfonic acid functionalized siloxane;
   b) neutralizing the acid;
   c) adding an oxirane compound to react with the in intermediate product of step b) to obtain an oxirane-functionalized ionic silicone compound;
   d) reacting the oxirane-functionalized ionic silicone compound of step c), oxirane ring-opening polymerization catalyst, a carrier solvent; and optionally, one or more silicon hydride activators to obtain an ionically-modified cross-linked silicone network by the ring-opening polymerization of oxirane moiety with hydride;
   e) shearing the ionically-modified cross-linked silicone network of step d) during and/or after polymerization of step d) with at least an carrier solvent to form an ionically-modified cross-linked silicone network gel; and
   f) adding the ionically-modified cross-linked silicone network gel of step d) to an oil phase of a personal care composition;
   wherein the oxirane-functionalized ionic silicone compound obtained in step c) has the general formula (I):

$$M^1{}_a M^2{}_b M^3{}_c D^1{}_d D^2{}_e D^3{}_f T^1{}_g T^2{}_h T^3{}_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$
where $R^1$, $R^2$, $R^3$, $R^5$, $R^6$, $R^8$, $R^9$, $R^{10}$, $R^{11}$, $R^{13}$, $R^{15}$, $R^{16}$ are aliphatic, aromatic or fluoro containing monovalent hydrocarbon radicals containing from 1 to 60 carbon atoms;
where $R^4$, $R^{12}$, $R^{17}$ are monovalent or multivalent radical bearing ionic group(s),
where $R^7$, $R^{14}$ and $R^{18}$ are independently selected from hydrogen, —$OR^{20}$ or hydrosilylation effective unsaturated monovalent radicals, wherein $R^{20}$ is selected from hydrogen, monovalent hydrocarbon radicals of from 1 to 60 carbon atoms,
where the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than 0.
2. The process of claim 1 wherein $R^4$, $R^{12}$, $R^{17}$ are each selected from the formula (II):

$$-A-I^{x-}M_n{}^{y+}; \quad (II)$$

where A is a spacing group having selected from a divalent hydrocarbon and hydrocarbonoxy group each containing from 1 to 60 carbon atoms, wherein the hydrocarbonoxy group contains at least one oxygen heteroatom,
where superscripts x and y are positive integers such to the proviso that and x is a product of n and y, and each subscript n independently has a value of from 1 to 6,
where I is an ionic group, where M is hydrogen or a cation independently selected from alkali metals, alkaline earth metals, rare earth metals, transition metals, metals, metal complexes, quaternary ammonium, polymeric cations or phosphonium groups; or,
zwitterions having the formula (III):

$$-R'-NR''_2{}^+-R'''-I \quad (III)$$

where R' is a divalent hydrocarbon radical containing from 1 to 60 carbon atoms,
where R" is monovalent hydrocarbon radical containing from 1 to 60 carbon atoms, and optionally, one or more of a sulfur atom, a nitrogen atom, oxygen atom, and
where R''' is divalent hydrocarbon radical containing from 2 to 20 carbon atoms; and, I is an ionic group.

3. The process of claim 1 wherein the subscripts in general formula (I) are such that $2 \leq a+b+c+d+e+f+g+h+i+j \leq 4000$.
4. The process of claim 1 wherein the subscripts in general formula (I) are such that $b+f+j > 1$.
5. The process of claim 1 wherein the oxirane-functionalized compound is of the general formula (IV):

$$M^2{}_{a'} M^H{}_{b'} M^E{}_{c'} M^I{}_{d'} D^2{}_{e'} D^H{}_{f'} D^E{}_{g'} D^I{}_{h'} T^2{}_{i'} T^H{}_{j'} T^E{}_{k'} T^I{}_{l'} Q_{m'} \quad (IV)$$

wherein:
$M^2 = R^{19} R^{20} R^{21} SiO_{1/2}$
$M^H = R^{23} R^{24} HSiO_{1/2}$
$M^E = R^{25} R^{26} R^E SiO_{1/2}$
$M^I = R^{27} R^{28} R^I SiO_{1/2}$
$D^2 = R^{29} R^{30} SiO_{2/2}$
$D^H = R^{31} HSiO_{2/2}$
$D^E = R^{32} R^E SiO_{2/2}$
$D^I = R^{33} R^I SiO_{2/2}$
$T^2 = R^{34} SiO_{3/2}$
$T^H = HSiO_{3/2}$
$T^E = R^E SiO_{3/2}$
$T^I = R^I SiO_{3/2}$
$Q = SiO_{4/2}$;
where $R^I$ is an ionic group, and $R^E$ is independently a monovalent hydrocarbon radical containing at least one oxirane moiety, which contains from 2 to 60 carbon atoms;
$R^{19}$, $R^{20}$, $R^{21}$, $R^{29}$, $R^{30}$ and $R^{34}$ are independently monovalent hydrocarbon radicals having from 1 to 60 carbon atoms;
$R^{23}$, $R^{24}$, are $R^{31}$ independently hydrogen, or monovalent hydrocarbon radicals having from 1 to 60 carbon atoms;
$R^{25}$, $R^{26}$ and $R^{32}$ are independently $R^E$ or monovalent hydrocarbon radicals having from 1 to 60 carbon atoms;
$R^{27}$, $R^{28}$, and $R^{33}$ are independently $R^I$ or nmonovalent hydrocarbon radicals having from 1 to 60 carbon atoms;
and where the stoichiometric subscripts a', b', c', d', e', f', g', h', i', j', k', l' and m' are either zero or positive subject to the following limitations: $c'+g'+k' > 1$; $d'+h'+l' > 1$; and $b'+f'+j'$, if present, is greater than $c'+g'+k'$; and $3 \geq a'+b'+c'+d'+e'+f'+g'+h'+i'+j'+k'+l'+m' \leq 6000$; and, with the proviso that $b'+f'+j' > 1$ when silicone hydride activator is absent and wherein the crosslinked ionic silicone network is formed by the ring-opening polymerization of oxirane moiety.
6. The process of claim 1 wherein at least one of $R^7$, $R^{14}$ and $R^{18}$ is selected from hydrogen.
7. The process of claim 1 wherein the carrier solvent comprises an ionically-modified silicone polymer having the general structure (V):

$$M^3{}_{\alpha'} M^4{}_{\beta'} D^3{}_{\chi'} D^4{}_{\delta'} T^3{}_{\epsilon'} T^4{}_{\phi'} Q_{\gamma'} \quad (V)$$

wherein:
$M^3 = R^1R^2R^3SiO_{1/2}$
$M^4 = R^4R^5R^I SiO_{1/2}$
$D^3 = R^6R^7 SiO_{2/2}$
$D^4 = R^8R^I SiO_{2/2}$
$T^3 = R^9 SiO_{3/2}$
$T^4 = R^{10} SiO_{3/2}$
$Q = SiO_{4/2}$, and wherein, the radicals $R^1$, $R^2$, $R^3$, $R^4$, $R^5$, $R^6$, $R^7$, $R^8$, $R^9$ and $R^{10}$ are independently selected from aliphatic or aromatic monovalent hydrocarbon radicals having from 1 to 60 carbon atoms, and optionally each Containing at least one hetero atom, wherein at least one $R^I$ is an ionic group, and the subscripts $\alpha'$, $\beta'$, $\chi'$, $\delta'$, $\epsilon'$, $\phi'$, and $\gamma'$ are zero or positive subject to the following limitations: $2 \leq \alpha' + \beta' + \chi' + \delta' + \epsilon' + \phi' + \gamma' \leq 6000$; and, $\beta' + \delta' + \phi' > 0$.

8. The process of claim 1 wherein the silicon hydride activator is of the general formula (VI):

$$M^3_\alpha M^H_\beta M^I_\chi D^3_\delta D^H_\epsilon D^I_\phi T^3_\gamma T^H_\eta T^I_\iota Q_\phi \quad (VI)$$

wherein:
$M^3 = R^{35}R^{36}R^{37}SiO_{1/2}$
$M^H = R^{38}R^{39}HSiO_{1/2}$
$M^I = R^{40}R^{41}R^I SiO_{1/2}$
$D^3 = R^{42}R^{43} SiO_{2/2}$
$D^H = R^{44}HSiO_{2/2}$
$D^I = R^{45}R^I SiO_{2/2}$
$T^3 = R^{46}SiO_{3/2}$
$T^H = HSiO_{3/2}$
$T^I = R^I SiO_{3/2}$
$Q = SiO_{4/2}$; and where
$R^{35}$, $R^{36}$, $R^{37}$, $R^{42}$, $R^{43}$ and $R^{46}$ are independently monovalent hydrocarbon radicals having from 1 to 60 carbon atoms;
$R^{38}$, $R^{39}$ and $R^{44}$ are independently hydrogen or monovalent hydrocarbon radicals having from 1 to 60 carbon atoms;
$R^{40}$, $R^{41}$ and $R^{45}$ are independently $R^I$ or monovalent hydrocarbon radicals having from 1 to 60 carbon atoms,
and where the stoichiometric subscripts $\alpha$, $\beta$, $\chi$, $\delta$, $\epsilon$, $\phi$, $\gamma$, $\eta$, $\iota$ and $\phi$ to are either zero or positive subject to the following limitations: $2 \leq \alpha + \beta + \chi + \delta + \epsilon + \phi + \gamma + \eta + \iota + \phi \leq 6000$; $\beta + \epsilon + \eta > 1$; and $\chi + \phi + \iota \geq 0$;
and wherein the crosslinked ionic silicone network is formed by the ring-opening polymerization of oxirane moiety.

9. The process of claim 1 wherein the oxirane ring-opening polymerization-effective catalyst is selected from the group consisting of platinum compounds, metal salts and acid catalysts and its derivatives that are capable of polymerizing an epoxy group.

10. The process of claim 9 wherein the acid catalyst capable of polymerizing an epoxy group is selected from onium salt generated acids; metal salts selected from the group consisting of aluminum trichloride and ferric chloride; lanthium triflates; and platinum compounds.

11. The process of claim 1 wherein the carrier solvent is at least one selected from silicone fluids, hydrocarbon fluids, esters, alcohols, fatty alcohols, glycols, organic waxes and organic oils.

12. The process of claim 1 wherein the crosslinked ionic silicone network is swelled by the carrier solvent.

13. The process of claim 12 wherein the carrier solvent is a hydrophilic emollient selected from the group consisting of glycerine, sorbitol, aqueous solution of moisturizing additives and combinations thereof.

14. The process of claim 1 where the silicon hydride activator is, a Si—H functional linear polysiloxane polymer represented by the formula:

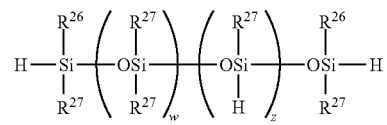

wherein $R^{26}$ and $R^{27}$ are each independently a monovalent hydrocarbon radical of from 1 to 60 carbon atoms; "w" is front 0 to 1,000; and "z" is from 0 to 200; or,
the silicon hydride activator is a cyclic silicone hydride represented by the formula:

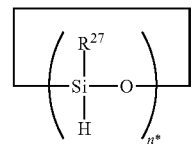

wherein $R^{27}$ is as defined above and "n*" is from 3 to 12.

15. The process of claim 1 wherein the crosslinked ionic silicone network is compatible with a particulate additive.

16. The process of claim 15 wherein the particulate additive is selected from inorganic particulates, polymeric latexes, and pigments.

17. A process of claim 1 wherein the carrier solvent is water.

18. The process of claim 1 wherein the composition is a homogenous system selected from aqueous or non-aqueous formulations.

19. The process of claim 1 wherein the composition comprises two or more non-miscible phases.

20. The process of claim 19 wherein the non-miscible phases are selected from the group consisting of aqueous, non-aqueous, solid particulates and combinations thereof.

21. The process of claim 1 wherein the crosslinked ionic silicone network gel can bind and release cosmetic actives.

22. A personal care application comprising the personal care composition prepared by the process of claim 1 wherein the personal care application is selected from the group consisting of deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products, protective creams, color cosmetics and other personal care formulations where silicone components have been conventionally added, as well as drug delivery systems for topical application of medicinal compositions that are to be applied to the skin.

23. A process of preparing a personal care composition wherein the personal care composition comprises at least an oil phase, and is made by the process comprising adding an ionically-modified cross-linked silicone network gel to the oil phase of the personal care composition wherein the ionically-modified cross-linked silicone network gel is made by:

(a) reacting a molecule having the general formula (Ia):

$$M_a M^H_b M^I_d D_e D^H_f D^I_h T_i T^H_j T^I_l Q_m \quad (Ia)$$

wherein:
$M^3 = R^{35}R^{36}R^{37}SiO_{1/2}$
$M^H = R^{38}R^{39}HSiO_{1/2}$
$M^I = R^{40}R^{41}R^I SiO_{1/2}$
$D^3 = R^{42}R^{43}SiO_{2/2}$
$D^H = R^{44}HSiO_{2/2}$
$D^I = R^{45}R^I SiO_{2/2}$
$T^3 = R^{46}SiO_{3/2}$
$T^H = HSiO_{3/2}$
$T^I = R^I SiO_{3/2}$
$Q = SiO_{4/2}$; and where
$R^{35}$, $R^{36}$, $R^{37}$, $R^{42}$, $R^{43}$ and $R^{46}$ are independently monovalent hydrocarbon radicals having from one to sixty carbon atoms;
$R^{38}$, $R^{39}$ and $R^{44}$ are independently hydrogen or monovalent hydrocarbon radicals having from one to sixty carbon atoms;
$R^{40}$, $R^{41}$ and $R^{45}$ are independently $R^I$ or monovalent hydrocarbon radicals having from one to sixty carbon atoms, where $R^I$ is a monovalent or multivalent radical bearing ionic group(s), and where the stoichiometric subscripts a, b', d, e, f', h, i, j', l and m are either zero or positive subject to the following limitations: $2 \geq a+b'+d+e+f'+h,+i+j'+l+m \leq 6000$; $b+f+j>1$; and $d+h+l \geq 0$;

with an olefinically unsaturated molecule containing one or more oxirane moieties, and polymerizing the reaction product of step (a) by epoxy ring-opening polymerization with the hydride moiety in the presence of an (ii) oxirane ring-opening polymerization catalyst, (iii) a carrier solvent, and, (iv) optionally a silyl-hydride molecule to produce the crosslinked ionic silicone network, provided, wherein the silyl-hydride molecule (iv) is absent, the molar amount of olefinic unsaturated moiety in the olefinically unsaturated molecule containing one or more oxirane moieties of step (a) is less than the molar amount of silyl hydride moiety in general formula (Ia); and, (b) shearing the reaction product of step (a) in the presence of at least one carrier solvent (iii) to provide the crosslinked ionic silicone network gel.

* * * * *